US008160678B2

(12) United States Patent
Cropper et al.

(10) Patent No.: US 8,160,678 B2
(45) Date of Patent: Apr. 17, 2012

(54) METHODS AND DEVICES FOR REPAIRING DAMAGED OR DISEASED TISSUE USING A SCANNING BEAM ASSEMBLY

(75) Inventors: Michael S. Cropper, Edgewood, KY (US); Thomas W. Huitema, Cincinnati, OH (US); Michael P. Weir, Blanchester, OH (US); Robert J. Dunki-Jacobs, Mason, OH (US); Jere J. Brophy, Loveland, OH (US); Robert M. Trusty, Cincinnati, OH (US); Randal T. Byrum, South Lebanon, OH (US); David C. Youmans, Loveland, OH (US); Sean P. Conlon, Loveland, OH (US); Gary L. Long, Cincinnati, OH (US); Paul G. Ritchie, Loveland, OH (US); Jane A. Sheetz, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 641 days.

(21) Appl. No.: 11/764,261

(22) Filed: Jun. 18, 2007

(65) Prior Publication Data
US 2008/0312490 A1  Dec. 18, 2008

(51) Int. Cl.
*A61B 5/05* (2006.01)
(52) U.S. Cl. ............ 600/427; 623/11; 623/17; 623/16; 623/902; 606/214
(58) Field of Classification Search ............... 600/427; 623/17, 11, 902, 16; 606/214
See application file for complete search history.

(56) References Cited

U.S. PATENT DOCUMENTS

| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |

(Continued)

FOREIGN PATENT DOCUMENTS
DE        3837248        5/1990
(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner* — Tse Chen
*Assistant Examiner* — Joel F Brutus
(74) *Attorney, Agent, or Firm* — Thompson Hine LLP

(57) ABSTRACT

A method for repairing or modifying an area of a patient's anatomy that comprises directing at least a portion of a scanning beam assembly to an area of a patient's anatomy, applying a radiation-responsive agent to portion of the anatomy, and exposing the radiation-responsive agent to radiation directed onto the agent by the reflector to cause the agent to therapeutically interact with the site. The scanning beam assembly including a radiation source capable of emitting radiation, a reflector that receives the radiation from the radiation source to direct the radiation onto the anatomy, wherein the reflector oscillates in at least two directions to create a scan of the anatomy, a detector to detect radiation returned from the anatomy, and a controller to convert the detected radiation into a displayable anatomy image.

48 Claims, 13 Drawing Sheets

U.S. PATENT DOCUMENTS

| | | |
|---|---|---|
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,464,013 A * | 11/1995 | Lemelson .................. 600/427 |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,951,543 A * | 9/1999 | Brauer .......................... 606/10 |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,989,244 A * | 11/1999 | Gregory et al. ................... 606/8 |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 * | 4/2001 | Lai .................................. 606/12 |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |

| Patent No. | Date | Inventor |
|---|---|---|
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,795,221 B1 | 9/2004 | Urey |
| 6,802,809 B2 | 10/2004 | Okada |
| 6,803,561 B2 | 10/2004 | Dunfield |
| 6,821,245 B2 | 11/2004 | Cline et al. |
| 6,845,190 B1 | 1/2005 | Smithwick et al. |
| 6,855,139 B2 * | 2/2005 | Ahle et al. ............ 606/8 |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel et al. |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |
| 7,391,013 B2 | 6/2008 | Johnston et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |

| | | | |
|---|---|---|---|
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |
| 2005/0020926 A1* | 1/2005 | Wiklof et al. | 600/476 |
| 2005/0023356 A1 | 2/2005 | Wiklof et al. |
| 2005/0030305 A1 | 2/2005 | Brown et al. |
| 2005/0038322 A1 | 2/2005 | Banik |
| 2005/0116038 A1 | 6/2005 | Lewis et al. |
| 2005/0162762 A1 | 7/2005 | Novak |
| 2005/0187441 A1 | 8/2005 | Kawasaki et al. |
| 2005/0203343 A1 | 9/2005 | Kang et al. |
| 2005/0240147 A1 | 10/2005 | Makower et al. |
| 2006/0010985 A1 | 1/2006 | Schneider |
| 2006/0084867 A1 | 4/2006 | Tremblay et al. |
| 2006/0122619 A1* | 6/2006 | Kablik et al. | 606/88 |
| 2006/0164330 A1 | 7/2006 | Bright et al. |
| 2006/0183246 A1 | 8/2006 | Wiesner et al. |
| 2006/0195014 A1 | 8/2006 | Seibel et al. |
| 2006/0212070 A1* | 9/2006 | Redmond et al. | 606/214 |
| 2006/0238774 A1 | 10/2006 | Lindner et al. |
| 2006/0245971 A1 | 11/2006 | Burns et al. |
| 2006/0284790 A1 | 12/2006 | Tegreene et al. |
| 2007/0005140 A1* | 1/2007 | Kim et al. | 623/17.16 |
| 2007/0038119 A1 | 2/2007 | Chen et al. |
| 2007/0046778 A1 | 3/2007 | Ishihara et al. |
| 2007/0135770 A1 | 6/2007 | Hunt et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173707 A1 | 7/2007 | Mitra |
| 2007/0179366 A1 | 8/2007 | Pewzner et al. |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2007/0260121 A1 | 11/2007 | Bakos et al. |
| 2007/0260273 A1 | 11/2007 | Cropper et al. |
| 2008/0033287 A1* | 2/2008 | Schwarze et al. | 600/427 |
| 2008/0058629 A1 | 3/2008 | Seibel et al. |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http:www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

"Custom Polarzing Cube Beamsplitters," from GlobalSpec The Engineering Search Engine, http://www.globalspec.com (date of first publication unknown).

Literature entitled "Dallas Semiconductor MAXIM—Visible-Laser Driver has Digitally Controlled Power Modulation," by Maxim Integrated Products, http://www.maxim-ic.com (Jul. 1, 2001).

"SCAN Mode Strategies for SCUBA-2" (May 25, 2005).

Seifert, M. et al., "High Power Diode Laser Beam Scanning in Multi-Kilowatt Range," Proceedings of the 23rd International Congress on Applications of Lasers and Electro-Optics (2004).

Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).

"Bladeless Trocars," by Johnson & Johnson, http://www.jnjgateway.com (date of first publication unknown).

Yeh, R. et al., "Microelectromechanical Components for Articulated Microrobots" (date of first publication unknown).

Xu, Q. et al., "Micrometre-scale silicon electro-optic modulator," Nature, vol. 435, pp. 325-327 (May 19, 2005).

Park, H. et al., "Development of Double-Sided Silicon Strip Position Sensor," 2005 IEEE Nuclear Science Symposium Conference Record, pp. 781-785 (2005).

Hammond, S.W., "Architecture and Operation of a Systolic Sparse Matrix Engine," Proceedings of the 3rd SIAM Conference on Parallel Processing for Scientific Computing, pp. 419-423 (1987).

Ra, H. et al., "Biomedical Optics & Medical Imaging—Microtechnology enables endoscopic confocal microscopy," SPIE (http://spie.org) (2007).

Invitation to Pay Additional Fees with Partial International Search Report, PCT/US2008/074275 (Jan. 16, 2009).

Invitation to Pay Additional Fees with Partial International Search Report, PCT/US2008/074273 (Dec. 30, 2008).

International Search Report issued regarding International Application No. PCT/US2007/078868 (Mar. 28, 2008).

PCT, International Search Report, PCT/US2008/056589 (Jul. 30, 2008).

PCT, International Search Report, PCT/US2008/059231 (Jul. 4, 2008).

PCT, International Search Report, PCT/US2007/087923 (May 21, 2008).

PCT, International Search Report, PCT/US2008/056596 (Jun. 23, 2008).

PCT, International Search Report, PCT/US2008/059235 (Jul. 14, 2008).

PCT, International Search Report, PCT/US2007/087930 (Jul. 3, 2008).

PCT, International Search Report, PCT/US2008/051274 (Jul. 18, 2008).

PCT, International Search Report, PCT/US2008/066552 (Oct. 23, 2008).

* cited by examiner

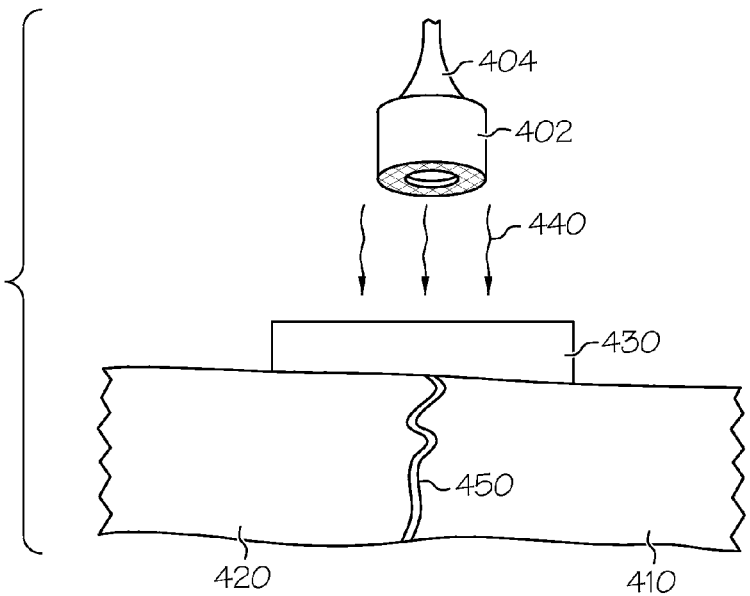
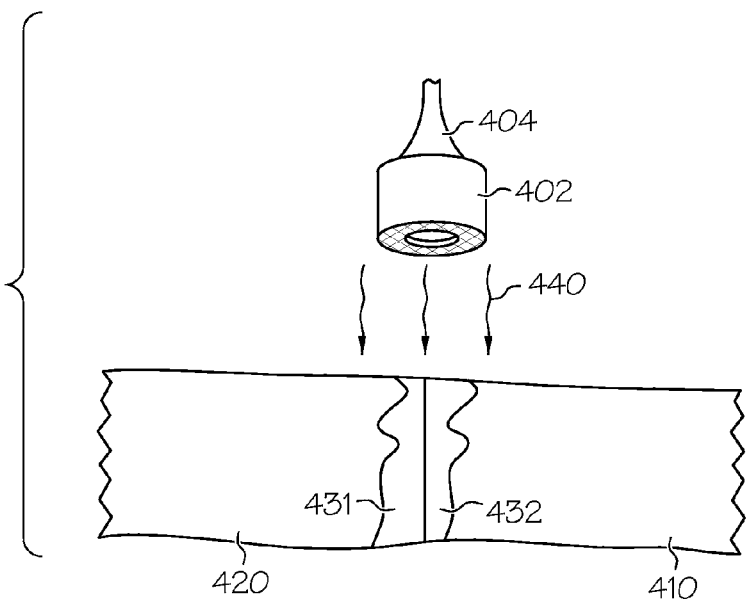

METHODS AND DEVICES FOR REPAIRING DAMAGED OR DISEASED TISSUE USING A SCANNING BEAM ASSEMBLY

FIELD OF THE INVENTION

The present invention is related generally to repairing or modifying damaged tissue within a body using a scanning beam unit.

BACKGROUND

The human body is complex and is often difficult for clinicians to examine internally to diagnose and treat a patient's illness. Cameras play an important part in modern medicine as a tool to aide clinicians in looking within a patient's body. Usually medical cameras are part of larger medical device, such as endoscopes, thermo-vision cameras, or laparoscopes. The cameras are usually digital, fiber optic, or pixelated sensor arrays. The cameras made with a pixelated sensor array may contain a single charge coupled assembly (CCD) or complimentary metal oxide semiconductor (CMOS) chip, or they may have multiple chips. The number of chips affects the size and resolution of the camera, and as a result limits where the camera can be used within the patient's body. There are therapeutic applications where smaller cameras or assemblies would be advantageous.

Recently, an assembly that can reach more remote areas within the body has been developed. This assembly is disclosed in United States Published Patent Application 2005/0020926. This assembly can be adapted to treat as well as to produce images of diseased or damaged tissue.

BRIEF SUMMARY

The present invention provides a method for repairing or modifying an area of a patient's anatomy that comprises directing at least a portion of a scanning beam assembly to an area of a patient's anatomy, applying a radiation-responsive agent to portion of the anatomy, and exposing the radiation-responsive agent to radiation directed onto the agent by the reflector to cause the agent to therapeutically interact with the site. The scanning beam assembly including a radiation source capable of emitting radiation, a reflector that receives the radiation from the radiation source to direct the radiation onto the anatomy, wherein the reflector oscillates in at least two directions to create a scan of the anatomy, a detector to detect radiation returned from the anatomy, and a controller to convert the detected radiation into a displayable anatomy image.

In one embodiment, the present invention provides a method for repairing an area of a patient's anatomy that comprises directing at least a portion of a scanning beam assembly to an area of a patient's anatomy, displaying an image of the anatomy, identifying a portion of the anatomy for the placement of a radiation-responsive agent, applying the radiation-responsive agent to the identified portion of the anatomy, and exposing the agent to radiation directed onto the agent to cause the agent to therapeutically interact with the anatomy. The scanning beam assembly including a radiation source capable of emitting radiation, a reflector that receives the radiation from the radiation source to direct the radiation onto the anatomy, wherein the reflector oscillates in at least two directions to create a scan of the anatomy, a detector to detect radiation returned from the area of the anatomy, and a controller to covert the detected radiation into a displayable anatomy image.

In another embodiment, the present invention provides a balloon catheter that comprises an expandable balloon, a catheter body having a plurality of lumens, wherein at least one lumen opens into the interior of the expandable balloon, and at least a portion of a scanning beam assembly. The scanning beam assembly including a radiation source capable of emitting radiation, a reflector that receives the radiation from the radiation source to direct the radiation onto the a patient's anatomy, wherein the reflector oscillates in at least two directions to create a scan of the anatomy, a detector to detect radiation returned from the anatomy, and a controller to covert the detected radiation into a displayable anatomy image.

In another embodiment, the present invention provides a method for repairing or modifying an area of a patient's anatomy that comprises directing at least a portion of a scanning beam assembly to an area of a patient's anatomy, displaying an image of the anatomy, identifying a portion of the anatomy where the radiation is to make a channel into the anatomy, and emitting the radiation to make the channel. The scanning beam assembly including a radiation source capable of emitting radiation, a reflector that receives the radiation from the radiation source to direct the radiation onto the a patient's anatomy, wherein the reflector oscillates in at least two directions to create a scan of the anatomy, a detector to detect radiation returned from the anatomy, and a controller to convert the detected radiation into a displayable anatomy image.

BRIEF DESCRIPTION OF THE SEVERAL VIEWS OF THE DRAWINGS

FIG. 21 illustrates an application of a tissue solder to be activated by the scanning module.

FIG. 22 illustrates an application of radiation-responsive tissue solder to bond inner surfaces of adjacent tissues.

DETAILED DESCRIPTION OF THE INVENTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. It is further understood that any one or more of the following-described embodiments, examples, etc. can be combined with any one or more of the other following-described embodiments, examples, etc.

Figure 1:
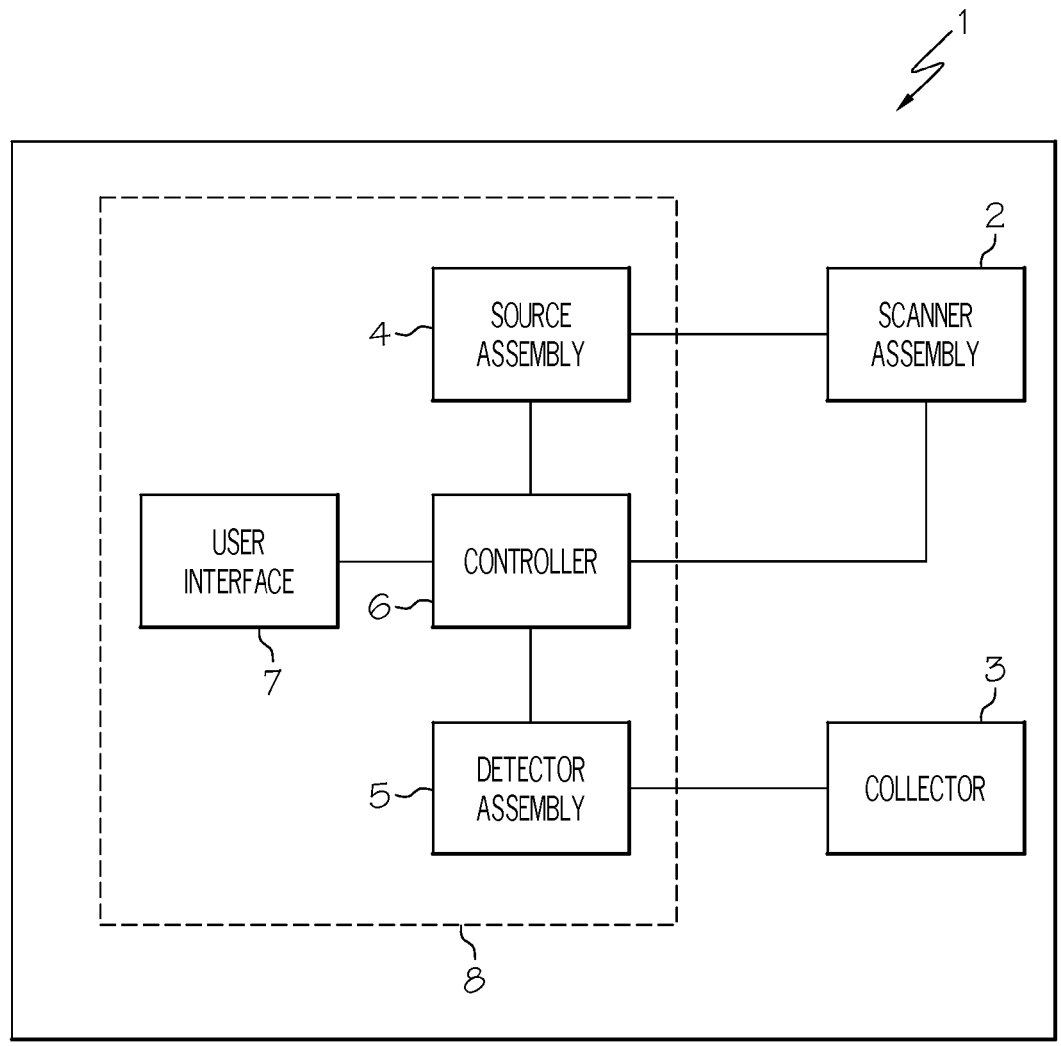
FIG. 1 is a block diagram of an embodiment of a medical device system including a scanner assembly.

Referring to FIG. 1, an embodiment of a scanning beam assembly 1, which may be part of a medical device, includes a scanner assembly 2, a collector 3, a radiation source assembly 4, a detector assembly 5, a controller 6 and a user interface 7. The radiation source assembly 4, detector assembly 5, controller 6 and user interface 7 make up functional element 8 that is known herein as a "console." The radiation source assembly 4, as selected by the user via the user interface 7, and acting through the controller 6, generates at least two wavelengths of radiation (e.g., in the visible wavelength range and/or otherwise). This radiation is conveyed in a beam to the scanner assembly 2, which causes the beam to be swept across a tissue surface. The extent of this swept area is generally known as the "field of view" (FOV). Radiation reflected from the scene within the FOV may be intercepted by the collector 3 and passed to the detector assembly 5. The detector assembly converts the received radiation to electrical signals that are then configured by the controller to form an image on a display assembly in the user interface 7.

Figure 2:
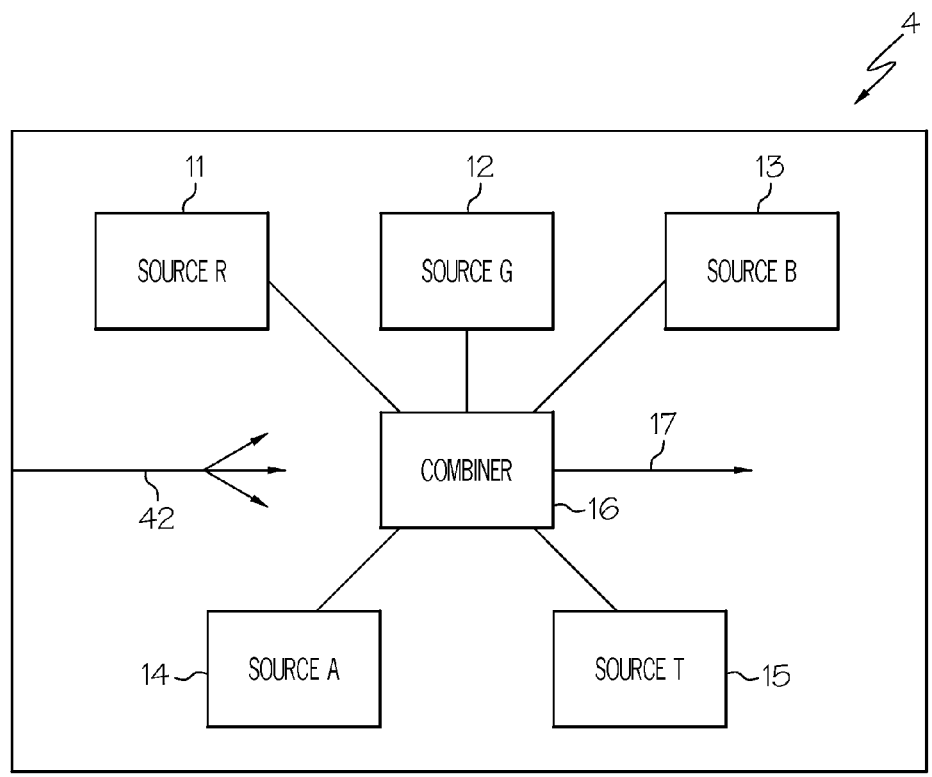
FIG. 2 is a block diagram of an embodiment of a source assembly including multiple sources for generating imaging, therapeutic and aiming beams.

FIG. 2 is a block diagram of one implementation of the source assembly 4. Source assembly 4 includes multiple sources, each capable of generating radiation at a selected wavelength. Five sources are shown here, numbered 11 thru 15. The outputs of the radiation sources 11-15 may, in some embodiments, be brought together in combiner element 16 to yield an output beam 17. Combiner 16 may also include beam-shaping optics such as one or more collimating lenses and/or apertures. The sources may be of various types such as, for instance, light emitting diodes (LEDs), lasers, thermal sources, arc sources, fluorescent sources, gas discharge sources, or others. Signals 42 may be provided by controller 6 (FIG. 1) to one or more of the sources and optionally the combiner 16. Signals 42 may optionally control wavelength, power, modulation or other beam properties.

The wavelength of radiation, for example, may be selected for imaging, therapy, or aiming. As used herein, an "imaging beam" refers to radiation selected for use in creating an image of a surface or region, a "therapeutic beam" refers to radiation selected to provide treatment of a condition such as diseased or damaged tissue, and an "aiming beam" refers to radiation selected to accentuate a portion of the FOV. The uses and application of such beams is disclosed in commonly assigned U.S. patent application Ser. No. 11/716,806 MEDICAL DEVICE INCLUDING SCANNED BEAM UNIT FOR IMAGING, THERAPY, AND/OR DIAGNOSIS as well as the operation of treatment mapping or selecting a treatment path. This reference is herein incorporated by reference in its entirety. In this example, sources 11, 12 and 13 emit red, green and blue radiation; source 14 emits an aiming beam at a wavelength selected to yield a distinct contrast to the typical target material; and source 15 emits a therapeutic beam at a wavelength that is highly absorbed and moreover can be efficiently generated at high power to treat diseased or damaged tissue. In some embodiments, the aiming beam may be provided by source separate from the therapeutic beam source 15. As an alternative, an aiming beam may be provided by source 15 as a reduced power therapeutic beam. In some embodiments, the aiming beam could be a virtual beam (i.e., a region in which one or more of the imaging sources is caused to increase (or decrease) significantly to create a bright (or dark) region in the displayed image.

In some embodiments, a source (not shown) provides a diagnostic beam. A "diagnostic beam" as used herein refers to radiation selected for analysis or detection of a disease or other medical condition including, for example, to visualize the presence of (or to activate) a diagnostic marker. The diagnostic marker could be naturally occurring (e.g., auto or self fluorescence) or introduced as part of the diagnostic procedure (e.g., fluorescent dyes).

Use of an aiming beam may be preferred in some circumstances. As will be seen later, while the treatment beam may follow the same path as the imaging beam, it is not constrained to follow the same timing. An aiming beam, managed in the same way as the therapeutic beam though at lower power and in a visible wavelength, may help ensure that the treatment is applied where the user intends. Furthermore, it may be a requirement of certain industry or regulatory standards such as AAMI or IEC that where higher power lasers are employed, an aiming beam be provided.

It should be noted that while five sources are illustrated, there may be more or fewer emitters depending, for example, on the end use. In some embodiments, sources may be combined or capable of providing various types of energy. In some cases, filters may be used to filter the radiation. In some embodiments, sources 11, 12 and 13 comprise three lasers; a red diode laser, a green diode-pumped solid state (DPSS) laser, and a blue DPSS laser at approximately 635 nm, 532 nm, and 473 nm, respectively. While laser diodes may be directly modulated, DPSS lasers generally require external modulation such as an acousto-optic modulator (AOM) for instance. In the case where an external modulator is used, it is considered part of the radiation source assembly and not shown separately.

Figure 3:
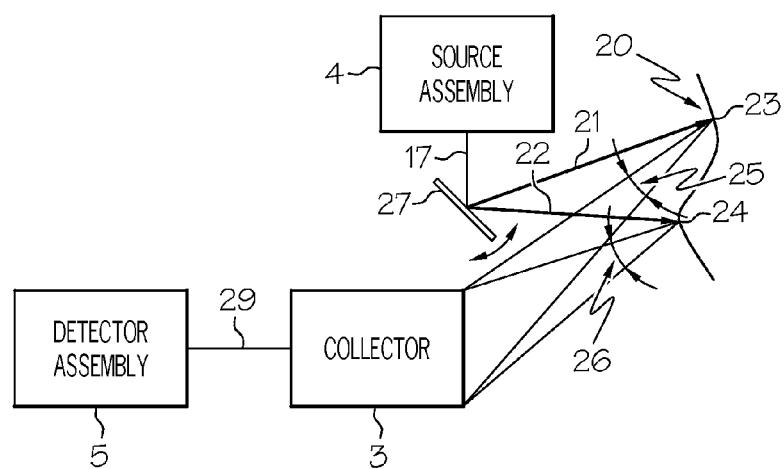
FIG. 3 is a block diagram illustrating radiation paths.

FIG. 3 illustrates the operation of an assembly 1 incorporating a scanner assembly 2. Reflector 27 receives a beam of radiation 17 from source assembly 4 and directs the beam onto the surface 20, for example, for one or more of imaging, therapy, or aiming purposes. At one point in time, the beam deflected by the reflector 27 is in direction shown as 21, and impinges upon the surface to illuminate a point 23. Reflector 27 oscillates in at least one axis (two axes in some embodiments), as indicated by the nearby arrowed arc, so that at some other point in time the deflected beam is in the direction indicated as 22 where, it illuminates point 24. Radiation is, in general, reflected, absorbed, scattered, refracted or otherwise affected by the properties of the surface. Radiation may leave the surface in many directions. The collector 3, however, may only capture that fraction of radiation which falls into the area subtended by its aperture. Regions 25 and 26 show the reflected radiation that is captured by the collector 3 when the beam is illuminating points 23 and 24 respectively. Directions 21 and 22 are not intended to represent any special part of the scan as the beam may be scanned using reflector 27 beyond them, and scans all points between them as well. Furthermore, a simplified two-dimensional view is represented by FIG. 3, and in general reflector 27 and collector 3 are adapted to illuminate and capture from surfaces occupying space in three dimensions.

Some embodiments use a micro-electromechanical (MEMS) scanner reflector to direct the imaging, aiming and therapeutic beams onto the surface. MEMS scanner reflectors are described in, for example, U.S. Pat. No. 6,140,979, entitled SCANNED DISPLAY WITH PINCH, TIMING, AND DISTORTION CORRECTION; U.S. Pat. No. 6,245,590, entitled FREQUENCY TUNABLE RESONANT SCANNER AND METHOD OF MAKING; U.S. Pat. No. 6,285,489, entitled FREQUENCY TUNABLE RESONANT SCANNER WITH AUXILIARY ARMS; U.S. Pat. No. 6,331,909, entitled FREQUENCY TUNABLE RESONANT SCANNER; U.S. Pat. No. 6,362,912, entitled SCANNED IMAGING APPARATUS WITH SWITCHED FEEDS; U.S. Pat. No. 6,384,406, entitled ACTIVE TUNING OF A TORSIONAL RESONANT STRUCTURE; U.S. Pat. No. 6,433,907, entitled SCANNED DISPLAY WITH PLURALITY OF SCANNING ASSEMBLIES; U.S. Pat. No. 6,512,622, entitled ACTIVE TUNING OF A TORSIONAL RESONANT STRUCTURE; U.S. Pat. No. 6,515,278, entitled FREQUENCY TUNABLE RESONANT SCANNER AND METHOD OF MAKING; U.S. Pat. No. 6,515,781, entitled SCANNED IMAGING APPARATUS WITH SWITCHED FEEDS; U.S. Pat. No. 6,525,310, entitled FREQUENCY TUNABLE RESONANT SCANNER; and U.S. patent application Ser. No. 10/873,540, entitled SCANNING ENDOSCOPE; all of which are hereby incorporated by reference in their entirety as if fully set forth herein.

Figure 4:
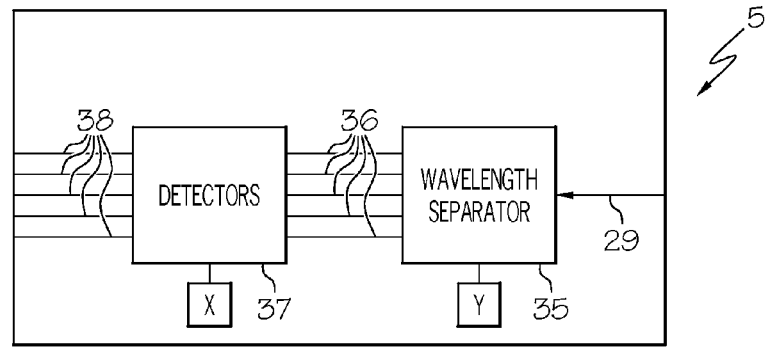
FIG. 4 is a block diagram of an embodiment of a detector assembly.

FIG. 4 is a block diagram of the exemplary detector assembly 5. Radiation 29 that is intercepted by the collector 3 is passed to the detector assembly 5. This radiation includes energy at several wavelengths, corresponding to those emitted by the source assembly 4, and possibly also including other wavelengths as may result from nonlinear processes (such as fluorescence). In some embodiments, wavelength separator 35 separates the incoming radiation 29 into pathways 36. Such separation may be performed by filters, gratings, or other devices. In an alternate configuration, wavelength separation may be incorporated in the collector 3, and separated wavelengths brought to the detectors 37, each in its own fiber or fiber bundle. Each separated wavelength of radiation is then sent to detectors 37 in the detector assembly 5. Such detectors may be physically separate, or parts of a common detector such as a CCD or CMOS device. Multiple detectors 37 may be incorporated for each wavelength. The detectors output electrical signals 38 corresponding the power, amplitude, or other characteristic of each wavelength of radiation detected. The signals can be used by a controller 6 (FIG. 6) to generate a digital image, e.g., for processing, decoding, archiving, printing, display, etc.

In some embodiments, X represents an input to the detectors 37 capable of modifying the transfer function from radiation to electric signals. Exemplary modifications may include adjustment of gain or offset or both. Y may represent an input to the wavelength separator 35 capable of modifying the transfer function therethrough. The modifying elements X and Y may be disposed to operate on the input to the respective detectors 37 and wavelength separator 35, acting on all or a subset of wavelengths received, at the outputs of the respective detectors 37 and wavelength separator 35 or at both inputs and outputs.

Figure 5:
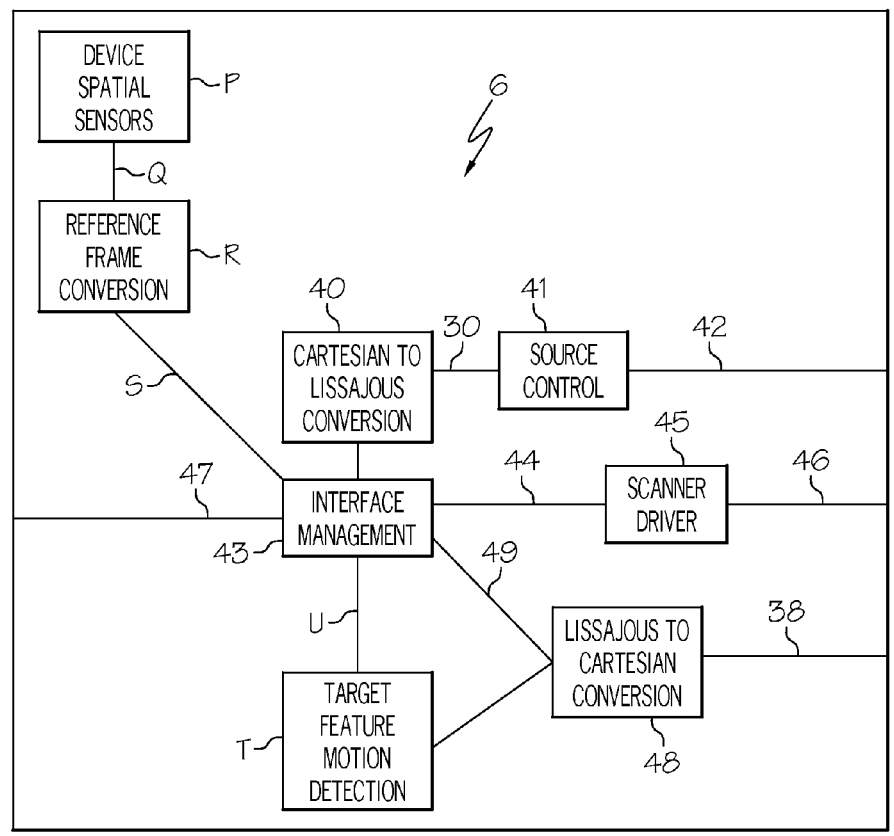
FIG. 5 is a block diagram of an embodiment of a controller for a medical device including a scanner assembly.

FIG. 5 is a block diagram of the exemplary controller 6. An interface management component 43, among other tasks, accepts operating mode commands from the user, illustrated as part of path 47. Such commands may include imaging and treatment modes, FOV and/or aspect ratio of the image, image storage, etc. Specifications related to the FOV and aspect ratio result in parameters sent via path 44 to a scanner driver 45, which generates requisite drive signals 46 to the reflector 27 (FIG. 3). The user may also specify treatment parameters, such as the location, shape and size of a region to be treated, the wavelength to be used, and duration of exposure. These result in parameters being sent to a coordinate converter 40, which converts the specifications into selection and modulation commands 30 to a source control block 41. This source control and modulation block 41 drives the source assembly 4 to provide the requisite radiation outputs 42. Signals 38 from the detector assembly 5 are converted from their scan coordinate system to a Cartesian form 49 at block 48 for display and sent to the interface management block 43 for user viewing.

In some embodiments, motion sensing is incorporated within the system via target feature motion detection, element T. For example, element P may include a number of sensors attached or connected to the scanner assembly 2. The sensors may sense location, orientation or both. The sensors may be, for example, accelerometers, magnetometers, rate gyros, electromagnetic position sensors, etc. Element Q represents the location and orientation signals generated by the sensors and element R represents a mathematic operation capable of converting the signals Q into a stationary reference frame. Element S represents output of element R which is used to modify the relationship of a displayed image to the scanned data 49 to compensate for sensed movement.

Element R operates on the scanned data 49 to detect the relative movement and provides signals U indicating magnitude and direction of the movement. This image tracking functionality may provide reliable treatment of the body which might be moving due to, for example, respiration, circulation or other biological activity.

Figure 6:
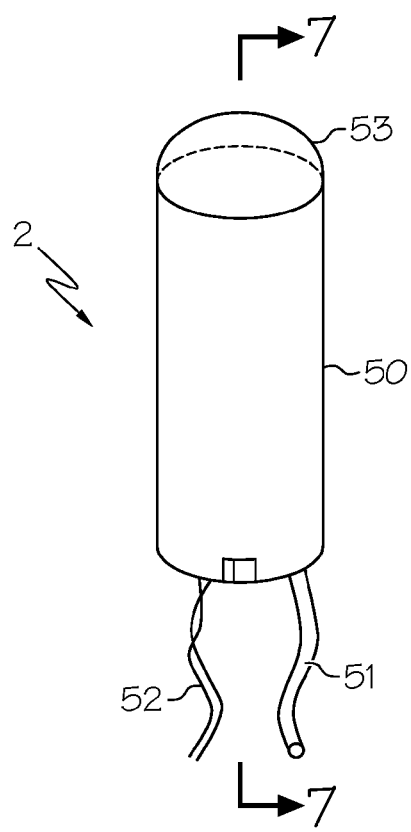
FIG. 6 is a perspective view of an embodiment of a scanner assembly.

FIG. 6 is an external view of one embodiment of the scanner assembly 2. Scanner assembly 2 includes a housing 50 that encloses the reflector 27 and other components. A source fiber 51 is used to deliver energy from the source assembly 4 to the scanner assembly 2. Source fiber 51 may be a single mode optical fiber. In some embodiments, one or more fibers may be used to deliver imaging beams and one or more other fibers may be used to deliver a therapeutic beam (e.g., therapeutic beams having longer wavelengths, e.g., greater than 1700 nm and/or higher power). In certain embodiments, a different type of fiber, such as a holey fiber, may be used to transmit energy from the source assembly 4. In some embodiments, the same optical fiber 51 is used to deliver both the imaging beams and the therapeutic beams to the reflector, the optical fiber defining a common path for both types of beams.

Electrical wires 52 convey drive signals for the reflector 27 and other signals (position feedback, temperature, etc.) to and from the scanner driver 45 (FIG. 5). Wires 52 may also provide control and feedback connections for controlling focus characteristics of the beam shaping optic 56. The distal end of the scanner assembly 2 is fitted with an optical element 53 which allows the scanned beam to pass out and illuminate the scene. This element 53 is generally referred to and illustrated as a dome; however, its curvature, contour, and surface treatments may depend on the application and optical properties required. In some embodiments, dome 53 provides a hermetic seal with the housing 50 to protect the internal elements from the environment.

Figure 7:
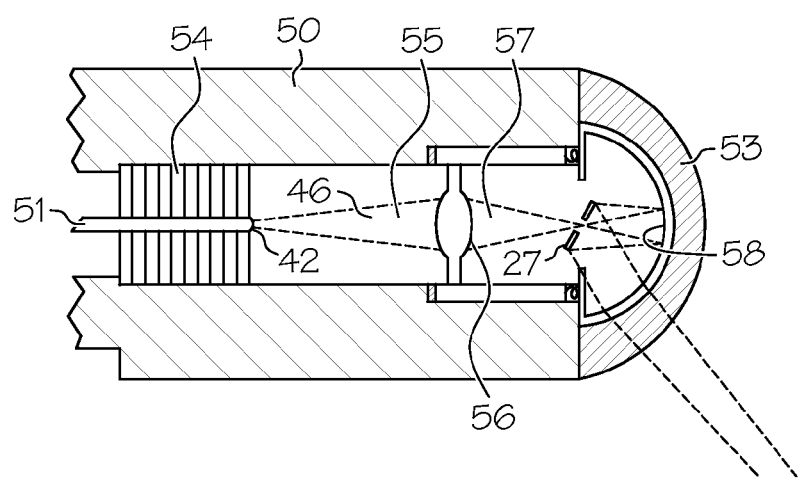
FIG. 7 is a side, section view of the scanner assembly of FIG. 6 along line 7-7.

FIG. 7 shows internal components of an embodiment of the scanner assembly 2. Source fiber 51 is affixed to the housing 50 using a ferrule 54. The end of the source fiber 51 may be polished to create a beam 55 of known divergence. The beam 55 is shaped by a beam shaping optic or lens 56 to create a beam shape appropriate for transmission through the system. After shaping, shaped beam 57 is fed through an aperture in the center of reflector 27, then reflected off a first reflecting surface 58. First reflecting surface 58 may have a beam shaping function. Beam 57 is then directed onto reflector 27 and then out of the scanner assembly 2, the details of which (in the case of an imaging beam) are described in U.S. patent application Ser. No. 10/873,540, entitled SCANNING ENDOSCOPE, the details of which are hereby incorporated by reference as if fully set forth herein. Any suitable materials can be used to form the reflector 27. In some embodiments, the reflective surface of the reflector 27 may be formed of gold or other suitable material for directing each of the beams including relative high energy therapeutic radiation. In other embodiments, a multilayer dielectric configuration may be used in forming reflector 27. In one embodiment, collecting fibers 63 may be included within housing 50.

Figure 8:
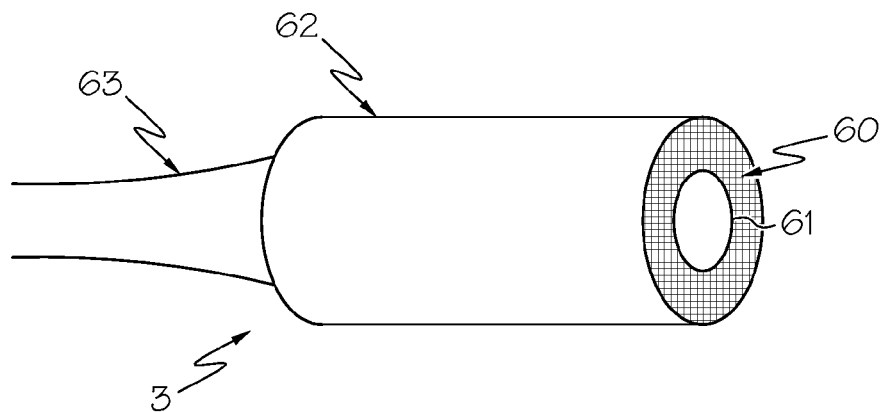
FIG. 8 is a perspective view of an embodiment of a radiation collector.

In another embodiment, as shown in FIG. 8, collector 3 may be configured to be installed coaxially with the scanner assembly 2. Radiation reflected from a scene impinges on the face 60 of the collector 3, which constitutes the receiving aperture. Face 60 is actually made up of the polished ends of a large number of small diameter, multimode collecting fibers 63 which conduct the radiation to the detector assembly 5. Scanner assembly 2 may be inserted into a central void 61. The collector 3 is enclosed by a housing 62. The fiber ends making up face 60 may be formed in a plane, or into other geometries to control the pattern of receiving sensitivity. They may be coated with diffusing or other materials to improve their angle of acceptance, to provide wavelength conversion, or wavelength selectivity. In some embodiments, the detector assembly 5 may be configured to form the receiving aperture and mounted in position to receive the reflected radiation directly, without the need for a separate collector 3.

Figure 9:
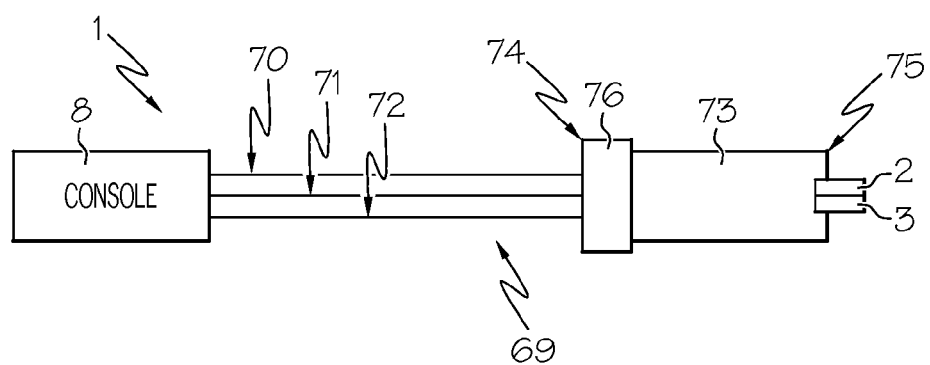
FIG. 9 is a perspective view of an endoscopic configuration of a medical device including a scanner assembly.

FIG. 9 shows diagrammatically various elements previously described as incorporated into an exemplary endoscope 69 for medical use. Endoscope 69 generally includes an elongate, rigid or flexible shaft 73 having a distal end 75 and a proximal end 74 opposite the distal end. There is typically a handle 76 which includes a number of controls, often both mechanical and electrical. In one embodiment, endoscope 69 includes scanning assembly 2 scanner assembly 2 and collector 3. Endoscope 69 may be connected to console 8 by source fibers 70, collection fibers 71, and electrical wiring 72. As used herein, an endoscope refers to an instrument for use in examining, diagnosing and/or treating tissue comprising a patient's body, either percutaneously or through a natural orifice or lumen. As used herein, the term "proximal" refers to a location on the medical device nearer to a user, and the term "distal" refers to a location that is nearer the patient. Typically, the console 8 of the medical device is located outside a patient's body and the distal end of the medical device is insertable into the patient's body. However, other configurations are possible. Furthermore, while an endoscope is referred to, any suitable type of medical device may be employed such as gastroscopes, enteroscopes, sigmoidoscopes, colonoscopes, laryngoscopes, rhinolaryoscopes, bronchoscopes, duodenoscopes, choledochoscopes, nephroscopes, cystoscopes, hysteroscopes, laparoscopes, arthroscopes, etc.

Figure 10:
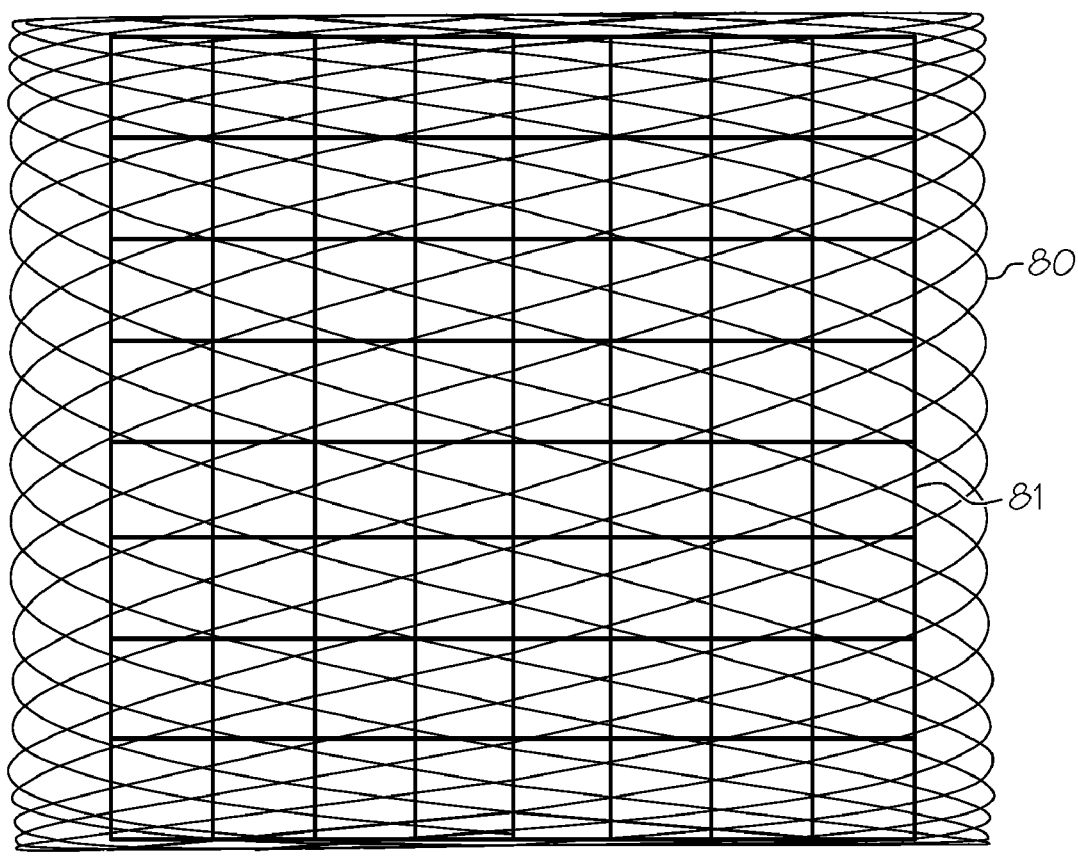
FIG. 10 is an illustration of a bi-sinusoidal scan pattern and a rectangular coordinate pattern plotted together.

Referring now to FIG. 10, as mentioned above, the reflector 27 scans the beam of radiation in a pattern. FIG. 10 shows an idealized bi-resonant or bi-sinusoidal scan pattern. High-speed MEMS reflectors and other resonant deflectors as described herein are configured and driven to execute sinusoidal angular deflections in two orthogonal axes, yielding the classical Lissajous pattern. Most current display devices are configured to address display data in a Cartesian form, for example as row and column, or a particular pixel along a nearly-horizontal scan line. The bi-resonant or Lissajous scan path 80 is shown overlaid with the Cartesian or rectilinear grid 81. In the illustrated instance, the intersections between the vertical and horizontal lines of the Cartesian grid 80 represent display pixel positions while the Lissajous trace 81 represents the actual path taken by the scanned spot. As the actual scan path does not align perfectly with all the rectilinear pixel positions, these image values may be determined through interpolation. In some embodiments, registration of the Lissajous trace 80 to the Cartesian grid 81 is based on a marker that links a reference point in the scan to a point in the rectilinear matrix.

Figure 11:
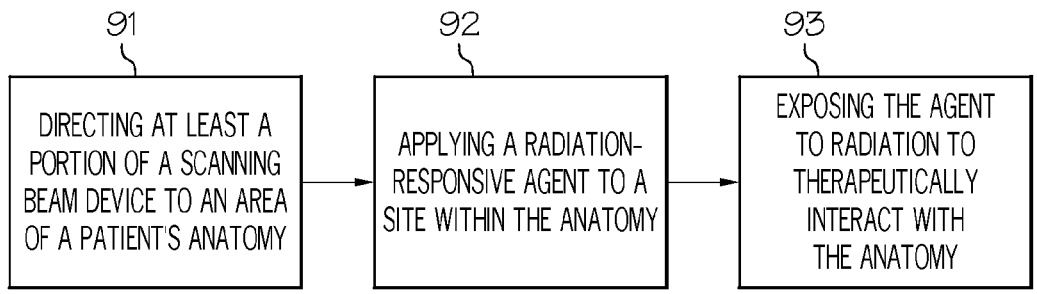
FIG. 11 is a flowchart illustrating a method for repairing or modifying an area of the anatomy.

In one embodiment, a user defines a treatment zone, border, or path by identifying the places within the image of the FOV where treatment is to be administered. The user may also select the parameters for the treatment such as the treatment beam wavelength, the power of the beam, and the duration of the exposure. The power of the beam may be modulated by a modulator to achieve the power selected by the user, as taught in commonly assigned U.S. patent application Ser. No. 11/716,911, titled POWER MODULATION OF A SCANNING BEAM FOR IMAGING, THERAPY, AND/OR DIAGNOSIS While the discussion below refers to radiation-responsive agents, such as adhesives or medical drugs, those skilled in the art will recognize that the techniques described herein can be used to activate any photo or radiation responsive agent useful in medical applications. Referring now to FIG. 11, the method comprises the steps of applying a radiation-responsive agent to a site within an area of a patient's anatomy 91, directing at least a portion of a scanning beam assembly to the anatomy 92, and exposing the agent to radiation directed onto the agent by the reflector to cause the agent to therapeutically interact with the anatomy 93. The step of applying a radiation-responsive agent 91 may occur before directing the scanning beam assembly to the anatomy 92, or after the scanning beam assembly has been directed to the anatomy. The scanning beam assembly may first be used to visualize and diagnose the area to be treated. The scanning beam assembly may include a radiation source capable of emitting one or more wavelengths of radiation, a reflector that receives the radiation from the radiation source to direct the radiation onto the anatomy, wherein the reflector oscillates in at least two directions to create a scan of the anatomy, at least one detector to detect radiation returned from the anatomy, and a controller to convert the detected radiation into a displayable image of the anatomy, as explained in greater detail above. The portion of the scanning beam assembly that is directed toward a portion of a patient's anatomy may include a medical guidewire to direct the assembly through the body. In another embodiment the scanning beam assembly may be part of a medical instrument.

The step of applying a radiation-responsive agent to the site 91 may be performed by any medical procedure or assembly that can successfully deliver the radiation-responsive agent to the site to be treated using the scanning beam assembly. In one embodiment, an applicator (i.e., a tube, sprayer, or the like) may be threaded down the working channel of endoscope or a laparoscope. In another embodiment, the applicator may be inserted through a trocar to apply the radiation-responsive agent. In yet another embodiment the radiation-responsive agent may be applied through a working channel or lumen within a catheter, balloon catheter, or the like. In one embodiment, the scanning beam assembly 1 is capable of curing all or selectively curing only a pre-determined portion of the agent the clinician indicates needs to be cured. The tool, assembly, or process chosen to apply the radiation-responsive agent will vary with the location within the body that needs to be reached for treatment, the radiation-responsive agent chosen, the form of the chosen radiation-responsive agent, and the size of the site to be treated.

The radiation-responsive agent may be any molecule, composition, or mixture capable of forming a biological, biocompatible, or biodegradable agent that does not cause adverse reaction in the tissue undergoing treatment. In another embodiment, the radiation responsive agent include a biocompatible coating that allows them to be safely placed within the patient's anatomy. The radiation-responsive agent may be a radiation curable molecule, compound, or composition. The radiation used to cure the radiation-responsive agent may be ultraviolet radiation, infrared, near infrared, or any other electromagnetic radiation. In one embodiment the radiation-responsive agent may be a medical adhesive that is capable of cross-linking when exposed to electromagnetic radiation. In another embodiment, the agent may be a medical drug that is activated by radiation. In another embodiment, the radiation-responsive agent is a shape-memory alloy. In another embodiment the radiation responsive agent may be a material that acts to promotes tissue welding or sealing, in the same manner as solder flux does with two pieces of metal.

The medical adhesive may be a gelatin or esterified gelatin as taught in U.S. Pat. No. 7,033,348, un-polymerized and polymerized type I and/or type III collagen compositions as taught in United States Published Application US2003/0032143, a composition of poly(L-lactic-co-glycolic acid), glycolic co-polymer, and bovine serum albumin as taught in United States Published Application US2004/0236371, a moiety containing a photosensitizing species and a protein or peptide as taught in U.S. Pat. No. 5,552,452, or any combination or mixture thereof. In another embodiment, to ensure that the medical adhesive cures when exposed to the radiation from the scanning beam assembly other molecules, compounds, or mixtures may be added to the agent.

In another embodiment the medical adhesive may be a proteinaceous biomolecule or a biological, biodegradable polypeptides as taught in U.S. Pat. Nos. 6,583,117 and 7,078,378. A proteinaceous biomolecule agent is a protein, which may be any protein or mixture of proteins. Examples of suitable proteins includes but is not limited to albumins, collagen, fibrinogen, tropoelastin, and elastin. Suitable proteins are typically those which can be cross-linked to form a matrix and which can be absorbed by the body. A biological, biodegradable polypeptides includes synthetic polypeptides incorporate light-absorbing material, such as a dye, into the agent, to improve energy absorption and cure. Examples of a suitable dyes include but are not limited to indocyanine green, methylene blue and fluorescein isothiocyanate. It will be understood that the light-absorbing material is chosen to be appropriate to the energy source that is used in forming tissue repairs involving the use of the medical adhesive.

The radiation-responsive agent may be a paste, gel, liquid, solid, pliable solid, powder, ribbon, mesh, film, metal or polymer scaffold or graft material. In one embodiment, a pliable radiation-responsive agent may be embedded into the spaces within a mesh or it may be applied as a covering to all or part of the mesh, stiffener or graft material. The pliable radiation-responsive agent may be shaped into various forms, such as tubular forms tapered or of uniform cross section. The tubular forms may be round or of ovoid profile, square crenulated, or any other geometric form. The radiation-responsive agent may be prepared in other shapes as required for the particular application to the treatment site including strips, patches, solid rods and hollow cubes with or without a flanged end. In another embodiment, the radiation-responsive agent composition may include medicinal drugs that aide in healing or treatment of the treatment site. The radiation-responsive agent referenced throughout the paragraphs below may be applied in any of the forms and may be any type of agent described above or combinations thereof.

The step of exposing the radiation-responsive agent with radiation emitted from the scanning beam assembly 93 may be carried out by selecting a desired wavelength, or plurality of wavelengths of radiation to be directed at the site where the radiation-responsive agent is applied. The scanning beam assembly 1 may have multiple lasers, light emitting diodes, thermal sources, arc sources, or fluorescent sources as source assembly 4. Any of sources 11-15 may also function as a therapeutic beam to cure the radiation-responsive agent. If sources 11-15 are not effective to cure the agent, then another source emitting the necessary cure radiation may be added to the assembly or substituted for one of these sources. As used herein, therapeutically interact includes, but is not limited thereto, when the agent bonds or adheres to the anatomy where the agent was applied, the agent cures or is cross-linked into a more rigid structure by the radiation, the agent expands to fill a void, the agent kills diseased tissue, the agent applies a medicine to promote healing, the agent forms a graft to the anatomy, the agent forms a stent within the anatomy, or the like.

The scanning beam assembly 1 may be connected to or configured with a display system that works in conjunction with a computer to plan and identify the site to be treated. A clinician may view the displayed image and then confirm and/or select a treatment path using the display, computer keyboard, or mouse. The treatment path corresponds to the tissue in need of treatment found within the site of visualization. For more details on selecting the treatment path see commonly assigned U.S. patent application Ser. No. 11/716,806 MEDICAL DEVICE INCLUDING SCANNED BEAM UNIT FOR IMAGING, THERAPY, AND/OR DIAGNOSIS, incorporated by reference above.

In another embodiment, it is possible that the computer can pre-determine the type of treatment based on optical information collected from the scene. For example, a dye may be used to stain particular tissue, then the computer may analyze the stains and suggest treatment options. In another embodiment, the computer can be programmed to automatically recognize certain tissue types, for example cancerous tissue, either via autofluorescence, impregnated dye fluorescence, or color-based analysis, and automatically select the zones in the scene that correlate to the targeted tissue. The computer would indicate to the physician the identified targets for confirmation. Once the clinician is satisfied with the treatment, they can move the scope to the next area to be treated.

The therapeutic beam or laser then cures the radiation-responsive agent along the treatment path, which enables the clinician to selectively treat only a portion of the radiation-responsive agent. A bioabsorbable radiation-responsive agent may be useful when the agent is cured selectively, in that any uncured agent may be absorbed by the body and not require the clinician to remove the excess. In one embodiment the laser treatment path may be followed continuously without visualization. In another embodiment, the laser treatment path may be interspersed with the visualization to allow the clinician to monitor the treatment progress. In yet another embodiment the scanning beam assembly 1 may be capable of treating and visualizing simultaneously. Additionally, the clinician may select whether the treatment is itself continuous or pulsated.

The method as described above for repairing a site within a body may be useful in closing gastric incisions, bonding two tissues together, soft tissue attachment, reconnecting tubular vessels, placing stents within body passageways, killing cancer cells or tumors, treating diseased tissue, or placing grafts within the body (such as intraluminal grafts). The reflector 27 of the scanning beam assembly 1 may vary in size, but are capable of being made smaller than the typical cameras. Reflector 27 may be held within a housing that is as small as about 3 to about 4 millimeters by about 4 millimeters to about 10 millimeters. This small size enables the scanning beam assembly to be carried on or in a catheter and threadedly delivered to visualize areas inside the lumen of the body or other hard to reach places, including but not limited to large veins and arteries. In some embodiments, scanner assembly 2, which includes reflector 27, may be included within the central void 61 of housing 62 shown in FIG. 8, to form a scanning module.

Figure 12:
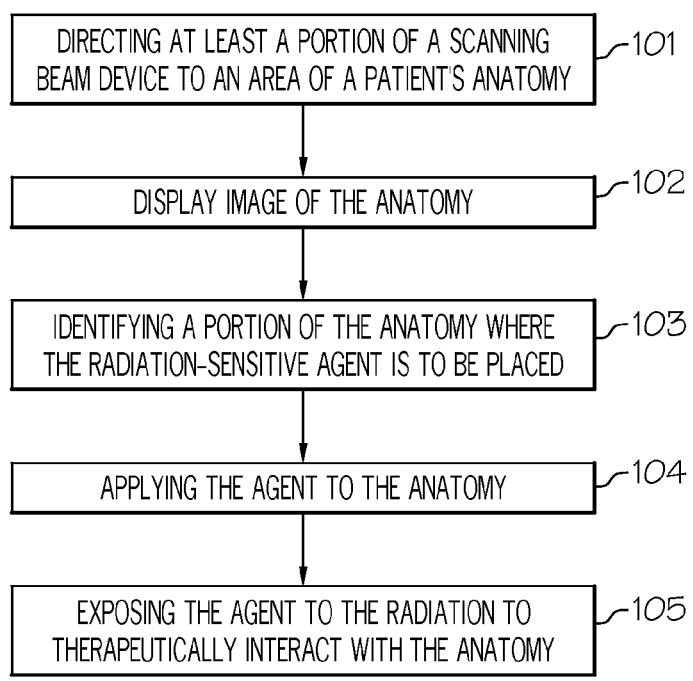
FIG. 12 is a flowchart illustrating another method for repairing or modifying an area of the anatomy.

In another embodiment, as illustrated in FIG. 12, a method for repairing an area of a patient's anatomy comprises the steps of directing at least a portion of a scanning beam assembly 1 to an area of a patient's anatomy 101, displaying an image of the anatomy 102, identifying a site within the anatomy for the placement a radiation-responsive agent 103, applying the radiation-responsive agent to the identified site using the display image 104, and exposing the agent to radiation directed onto the agent by a reflector 27, which is part of the scanning beam assembly 1 to cause the agent to therapeutically interact with the site 105. In another embodiment, the method further comprises the steps of directing a balloon catheter to the site, where a portion of the scanning beam assembly 1 is part of the balloon catheter, dispensing a radiation-responsive agent onto the balloon catheter, and expanding the balloon to apply the agent to the site.

Figure 13:
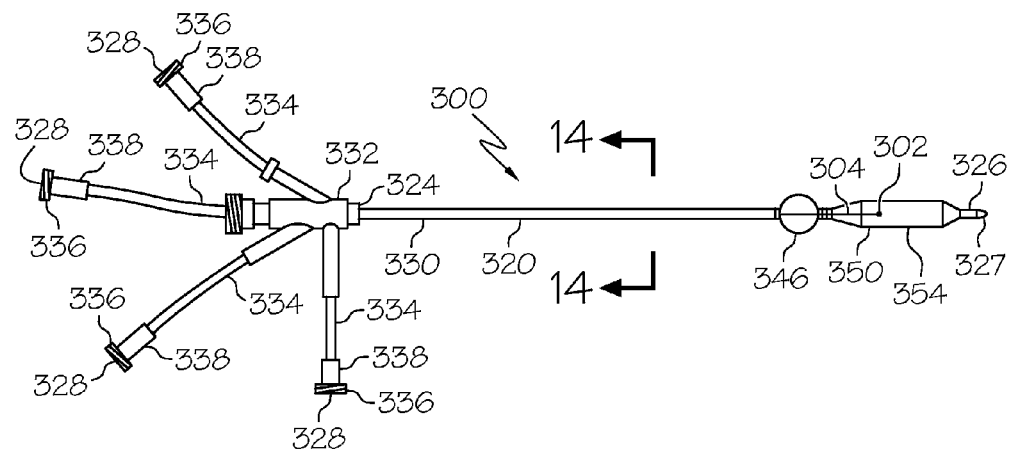
FIG. 13 is a side elevation view of a balloon catheter for use with a scan beam assembly.
Figure 14:
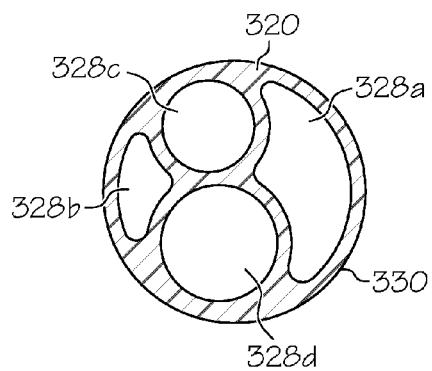
FIG. 14 is a transverse cross-section view of the catheter body of FIG. 13 taken along lines 14-14.

In one embodiment, the balloon may be similar to the balloon catheter taught in U.S. Pat. No. 6,056,721, as shown in FIG. 13 and designated by the reference numeral 300. The balloon catheter may be adapted for use with the scanning beam assembly 1. The balloon catheter 300 may include an elongate catheter body 320. This catheter body 320 may be a flexible or rigid, or semi-rigid tubular shaft having a proximal end 324 and a distal end 326. A plurality of longitudinally aligned interior passageways or lumens 328a, 328b, 328c, and 328d, as shown in FIG. 14, extend along the catheter body 320 from the proximal end 324. An outer surface or wall 330 surrounds the plurality of lumens 328a, 328b, 328c, and 328d and generally defines the elongate catheter body 320.

The distal end 326 preferably terminates at a distal tip 327. A hub 332 having a plurality of extension tubes 334 may be coupled to the proximal end 324 of the catheter body 320. The hub 332 may be adapted to be a hand piece when the balloon catheter 300 is used with the scanning beam assembly 1. Each of the extension tubes 334 may be connected with a respective one of the plurality of lumens 328a-328d such that each lumen 328a-328d is fluidly coupled or otherwise in open communication with an extension tube 334. A connecter 336, such as a luer lock, may be provided at a proximal end 338 of each extension tube 334. The detector may be a multi-mode optical fiber or an optical to electrical converter (i.e. a photodiode) that transmits the reflected signal.

In one embodiment, the balloon catheter 300 may have a first balloon 346. The first balloon 346 may be a round or semi-round balloon. The balloon 346 is preferably made from a flexible and bio-compatible material. These materials may include a rubber such as a medical grade latex, a silicone, polyurethane, polyethylene, polyethylene terephthalate, polyvinyl chloride, nylon and ionomers such as Surlyn, manufactured by the Polymer Products Division of the Du Pont Company. The first balloon 346 may act as a seal around a passageway or act as an anchor within the passageway.

In another embodiment, the balloon catheter 300 may have a second inflatable and deflatable angioplasty balloon 350. This second balloon 350 may have a central portion 354. The second balloon 350 may be made of any of the materials mentioned above, or any other material capable of being inflated and deflated by a fluid or gas. In one embodiment, the material may be any material capable of allowing radiation to pass through the material to activate a radiation-responsive agent contained on the outside of the second balloon 350. In one embodiment both the first and second balloon, 346 and 350 respectively, may be present as shown in FIG. 13, or in another embodiment their relative positions on the catheter body 320 may be reversed. In yet another embodiment, only the first balloon 346 may be present, or only the second balloon 350 may be present. Both the first balloon 346 and/or the second balloon 350 may have a variable inter-diameter.

In one embodiment, balloon catheter 300 contains connecting cable 304 and a scanning module 302. Scanning module 302 is a portion of scanning beam assembly 1, which in some embodiments includes scanner assembly 2 within the central void 61 of housing 62 including collectors 3 (shown in FIG. 8). Connecting cable 304 connects the scanning module 302 to the other portions of scanning beam assembly 1, shown in FIG. 1. In one embodiment, the scanning module 302 is inside the second balloon 350.

Scanning beam assembly 1 may include a display system on which a clinician may see the anatomy and determine how to treat a site within that area. To see an image when scanning module 302 is within the second balloon 350, second balloon 350 may be made of a material that allows the imaging wavelengths from the source assembly 4 to pass through the balloon material and likewise the returned radiation from the field of view pass back through the balloon material. In one embodiment, the scanning module 302 may be moved or directed while inside the second balloon 350 using the a hand piece or steering control that may be included as part of scanning beam assembly 1.

In another embodiment, scanning module 302 and connecting cable 304 may be external to the balloon catheter 300 in any location that will allow the radiation emitted from the scanning module 302 to reach the radiation-responsive agent to cure it or cause it to therapeutically interact with the tissue site. In one embodiment, the scanning module 302 may be near the distal tip 327 directing the scanning beam back at the second balloon 350, or in another embodiment the scanning module 302 may be between the first balloon 346 and the second balloon 350 directing the emitted radiation toward the second balloon 350. In another embodiment, mirrors may be used in conjunction with the scanning module 302 to direct the radiation around the second balloon.

Figure 15:
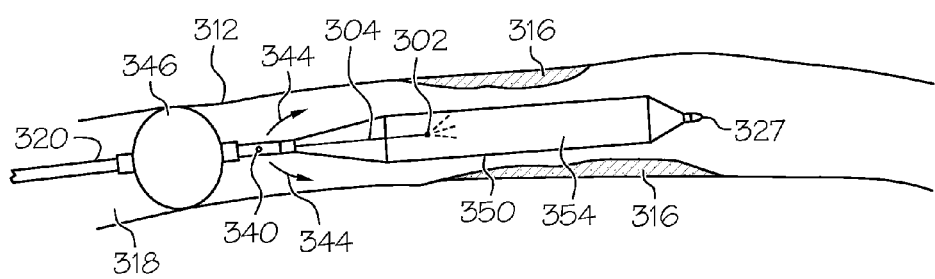
FIG. 15 is a perspective view of the balloon catheter of FIG. 13 shown with a scanning module inside the second balloon.

The step of dispensing a radiation-responsive agent onto the balloon catheter 320 may be carried out using an infusion port 340 in the catheter body 320 as shown in FIG. 15. The balloon catheter 300 may be inserted within a body passageway 312, which may include almost any body passageway, including a vascular conduit such as an artery, a vessel or a vein. An obstructing material 316 is shown constricting or otherwise obstructing a flow passageway 318.

In one embodiment, the infusion port 340 may be used to disperse a radiation-responsive agent 344 into the flow passageway 318 to cover the external surface of the second balloon 350. The infusion port 340 may be fluidly coupled to an infusion lumen 328a, as shown in FIG. 14. The infusion port 340 and infusion lumen 328a may be used to pass a medicine or drug, such as a radiation-responsive agent 344, from a supply pump attached to one of the balloon catheter's connectors 336 connected to the scanning beam assembly 1.

In one embodiment, the infusion port 340 may be a single oval, circular, or any other shaped port. In another embodiment, the infusion port 340 may be a plurality of openings or ports spaced uniformly or non-uniformly circumferentially around the catheter body 320. The spacing and placement of the plurality of infusion ports 340 may be such that the radiation-responsive agent when pumped through a lumen 328a will efficiently and effectively flow to cover the central portion 354 of the second balloon 350. The infusion lumen 328a may be connected in fluid communication with a working channel on a hand piece or a hose included as part of the scanning beam assembly 1. The working channel and/or hose may be used to force or pump the radiation-responsive agent toward the distal end 327 of the balloon catheter 300 such that the radiation-responsive agent 344 is pushed through the infusion port 340. The infusion lumen 328a should comprise a sufficiently large cross sectional area along the catheter body 320 to allow for passage of a large volume of the radiation-responsive agent. The infusion lumen 328a may also be configured with a circular, oval, square, trapezoidal, rhomboidal, or any other shaped cross section.

A second lumen 328b of the plurality of lumens 328a-328d extends from the proximal end 324 of the catheter body 320 and is fluidly connected to an opening or openings in the outer wall 330 of the catheter body 320 within the first balloon 346. The third lumen 328c of the plurality of lumens 328a-328d extends from the proximal end 324 of the catheter body 320 and is fluidly connected to an opening or openings in the outer wall 330 of the catheter body 320 within the second balloon 350. The fourth lumen 328d, may be configured for movably supporting a connecting cable 304 and scanning module 302.

In one embodiment, the radiation-responsive agent 344 may be passed through infusion lumen 328a, exiting from infusion port 340 disposed between the first balloon 346 and the second balloon 350. The radiation-responsive agent 344 may be infused at a pressure greater than the pressure within the angioplasty balloon 350 but less than the pressure within the first balloon 346. This allows the radiation-responsive agent 344 to exit the infusion port 340 into the sealed space between the first balloon 346 and the second balloon 350. The radiation-responsive agent 344 may then seep around the inflated central portion 354 of the second balloon 350. In one embodiment, the second balloon 350 may be completely deflated when the radiation-responsive agent 344 is applied.

In another embodiment, the second balloon 350 may be partially inflated when the radiation-responsive agent 344 is applied.

Figure 17:
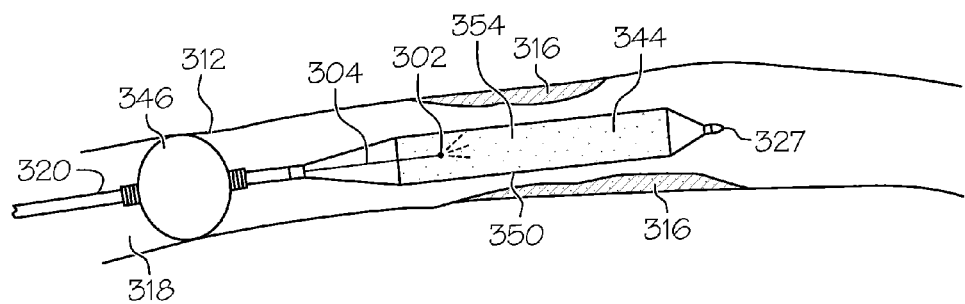
FIG. 17 is a perspective view of a balloon catheter shown with an radiation-responsive agent pre-applied to the second balloon.

In another embodiment, as shown in FIG. 17, the second balloon 350 may have a film or layer of agent radiation-responsive agent 344 film coating the outer surface of the central portion 354 prior to insertion of the balloon catheter 300 into a body passageway 312. The radiation-responsive agent film may be evenly circumferentially distributed around the second balloon 350. In another embodiment, the film or layer of radiation-responsive agent on the second balloon 350 may be a paste, mesh, graft, or gel on the outer surface of the central portion 354 of the balloon.

Figure 18:
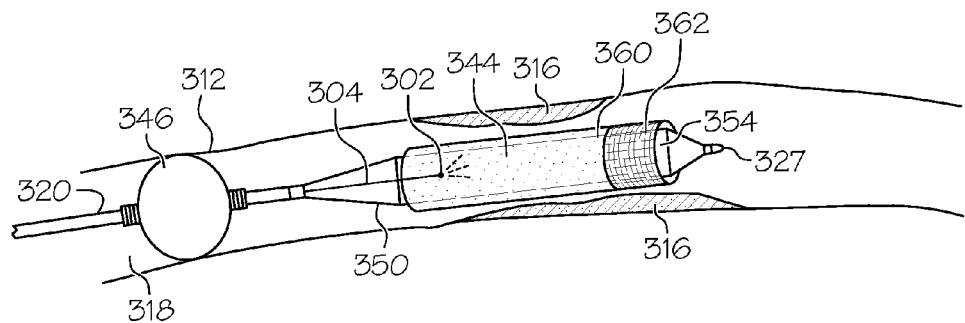
FIG. 18 is a perspective view of a balloon catheter shown with an annular sleeve of radiation-responsive agent on its surface.

In one embodiment, as shown in FIG. 18, the radiation-responsive agent 344 may comprise a continuous or substantially continuous annular sleeve 360. The annular sleeve 360 may be formed from a rectangular strip of radiation-responsive agent film that is rolled around the second balloon's 350 central portion 354 through one complete revolution, or two or more revolutions to provide multiple layers. The number of layers depends upon the thickness of the film and the desired amount of agent and the amount of radiation to be emitted at the site. In another embodiment, the annular sleeve 360 may be formed from a mesh 362 backing that is coated with a radiation-responsive agent 344.

Figure 19:
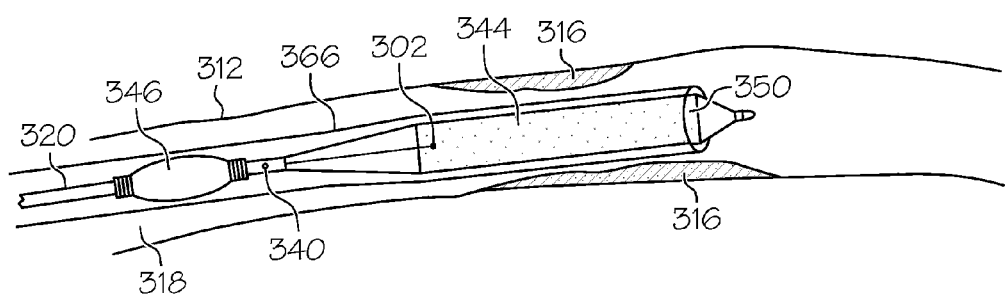
FIG. 19 is a perspective view of a balloon catheter including a cover.

The balloon catheters of the embodiment shown in FIGS. 17,18 may further include cover 366 illustrated in FIG. 19. Cover 366 protects the radiation-responsive agent 344 contained in the coating or annular sleeve 360 while the catheter 300 is being inserted into the body. Once the catheter 300 has been reached its destination within the body, cover 366 is either pulled back away from balloon or catheter 300 is advanced out of the cover 366.

Figure 20:
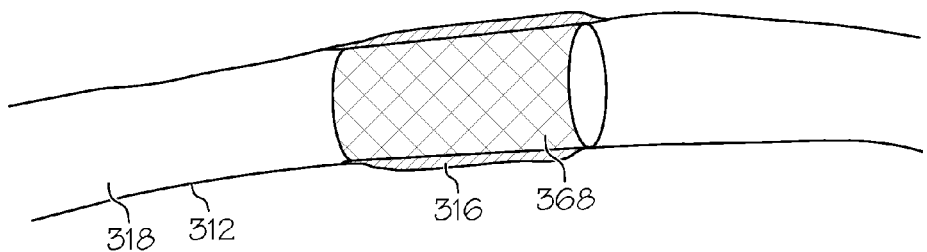
FIG. 20 is a perspective view of a stent formed by the method of FIGS. 11,12.

The second balloon 350 is then expanded to apply the radiation-responsive agent 344 to the site to be treated within body passageway 312. In this configuration, the radiation-responsive agent 344 is uniformly applied at a uniform pressure to the interior surface of the body passageway 312. Some of the radiation-responsive agent 344 may flows into any cracks, depressions, or tears within the body passageway 312 or obstructing material 316. The radiation-responsive agent 344 therapeutically interacts with the body passageway to bond to the tissue to stay in place, to treat diseased tissue, or to cure into a thin walled tubular member, known as a stent 368. Stent 368 is shown in FIG. 20 within body passageway 312 at the site of obstructing material 316, such that stent 368 is opening body passageway 312 where it was formerly constricted by obstructing material 316. Stent 368 may be made from any of the radiation-responsive agents described above. In some embodiments, stent 368 may be a bioabsorbable radiation-responsive agent so that no separate procedure is needed to remove stent 368. The radiation-responsive agent may be applied to the second balloon 350 such that stent 368 may have tubular walls of uniform thickness.

Then the radiation-responsive agent 344 is exposed to radiation emitted from the scan beam assembly's scanning module 302 to cure or cross-link the agent, as explained above. In one embodiment, the radiation-responsive agent 344 may be cured selectively such that the resulting stent 368 is a scaffold of cured agent similar to a metal self-expanding stent as shown in U.S. Pat. No. 5,545,211. In another embodiment the radiation-responsive agent 344 may be gradually cured or "grown" to a custom length by scanning the agent repeatedly using the method above while gradually moving the catheter along the anatomy. In one embodiment, the radiation-responsive agent of stent 368 is selectively cured to form a stent with slots throughout. The slots may be substantially parallel to a long axis of stent 368, perpendicular to the long axis, or a combination thereof.

In one embodiment, the radiation-responsive agent 344 is a bioabsorbable composition such that the resulting agent cured stent is a temporary stent that will be absorbed slowly by the body, which eliminates a second procedure to remove the stent. In another embodiment, the radiation-responsive agent 344 is a composition that is not bioabsorbable such that the resulting agent cured stent is a more permanent stent.

Bonding Separated Tissues

FIGS. 21,22 illustrate different embodiments for bonding separated tissues together by the application of a gel, film, mesh, paste, powder, ribbon, or solid radiation-responsive agent 430 and the curing due to exposure to radiation from scanning beam assembly 1. In one embodiment, scanning module 402, which is connected to scanning beam assembly 1 by connecting cable 404 is inserted within the area of the body to be exposed to radiation or is aligned with the area of the body to be exposed. The radiation-responsive agent 430 may be any of the agents listed above, or combinations thereof. In one embodiment, the radiation-responsive agent may include a catalyst to aid in absorbing the radiation and/or a glue to hold the agent into place prior to curing. First and second tissues 410 and 420 to be joined together are brought within close proximity with one another. The separation of the first and second tissues 410 and 420 may be a surgical incision, an accidental cut, a tear, or a separation of tissue interior to or exterior to the body.

In one embodiment, as shown in FIG. 21, a layer of gelatinized radiation-responsive agent 430 is provided overlaying the location where the tissues are to be joined. The radiation-responsive agent is overlaid using a balloon catheter as described, a sprayer, or any other method. The radiation-responsive agent 430 is then exposed to selected wavelengths of radiation 440 from the scanning module 402, which in one embodiment may be infrared light generated by a laser depending upon the chosen radiation-responsive agent 430. Upon activation by the radiation, the radiation-responsive agent 430 becomes less viscous and therefore flows, for example, into region 450 at the junction of the two tissues 410 and 420. The solder penetrates the interstices of tissues 410 and 420 and fills voids located in region 450. With further application of radiation, the radiation-responsive agent 430 cross-links to itself as well as cross-linking to the underlying tissues.

In another embodiment, as shown in FIG. 22, the radiation-responsive agent 430 may be applied to the inner surface of tissues 420 and 410, respectively as a first agent layer 431 and a second agent layer 432. Then the first and second agent layers 431 and 432 may be exposed to radiation from the laser 440 at the interface between tissues 410 and 420 to complete the bonding process.

In one embodiment, the laser light 440 emitted from the scanning module 402 is scanned across the tissue interface 450 from the first tissue 410 to the second tissue 420 then back to the first tissue 410 repeatedly along the length of the tissue interface 450. Scanning module 402 is a portion of scanning beam assembly 1, which in some embodiments includes scanner assembly 2 within the central void 61 of housing 62 including collectors 3 (shown in FIG. 8). In another embodiment the laser light 440 emitted starts at the second tissue 420 and scans across the tissue interface 450 to the first tissue 410 and back to the second tissue 420 repeatedly along the length of the tissue interface 450. In another embodiment, the tissue interface 450 is scanned along the length of the tissue interface 450 between the first and second tissues 410 and 420. In yet another embodiment, the laser light 440 scans across the tissue interface 450 as described above and is additionally scanned along the length of the tissue interface 450. The scanning laser light 440 cures the radiation-responsive agent 430 slowly and evenly. Multiple passes of the laser light 440 may be needed for complete curing.

In one embodiment, the laser light 440 may be a high power infrared laser. In another embodiment, the clinician may set a scanning treatment plan using a touch-screen input or computer as part of the scanning beam assembly 1. The scanning treatment plan may encompass any pattern of scanning, including those described above to cure all or a selected portion of the agent. The clinician may select the laser light 440 to be emitted as a continuous stream or as a pulse stream.

Shape Memory Alloy Stents

Figure 23:
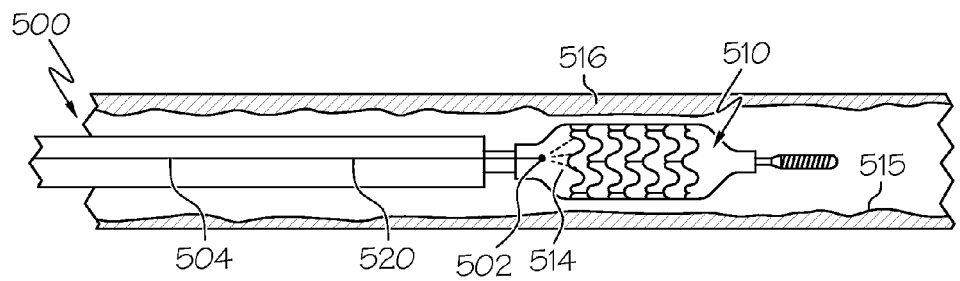
FIG. 23 is an elevational plan view wherein the stent is to be activated by the scan beam assembly.
Figure 24A:
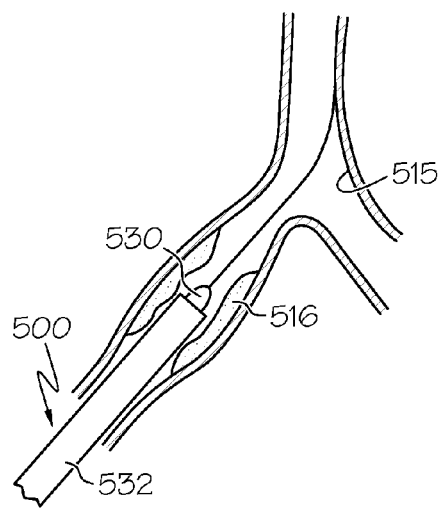
FIGS. 24A to 24D are views showing steps for implantation of a stent into a lumen, where the stent will be activated by a scan beam assembly.
Figure 24B:
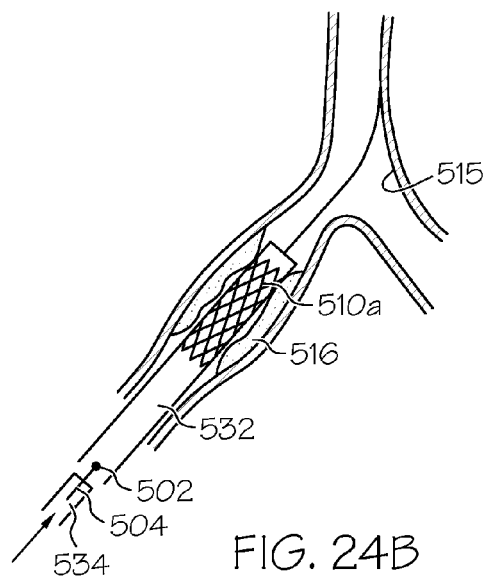
Figure 24C:
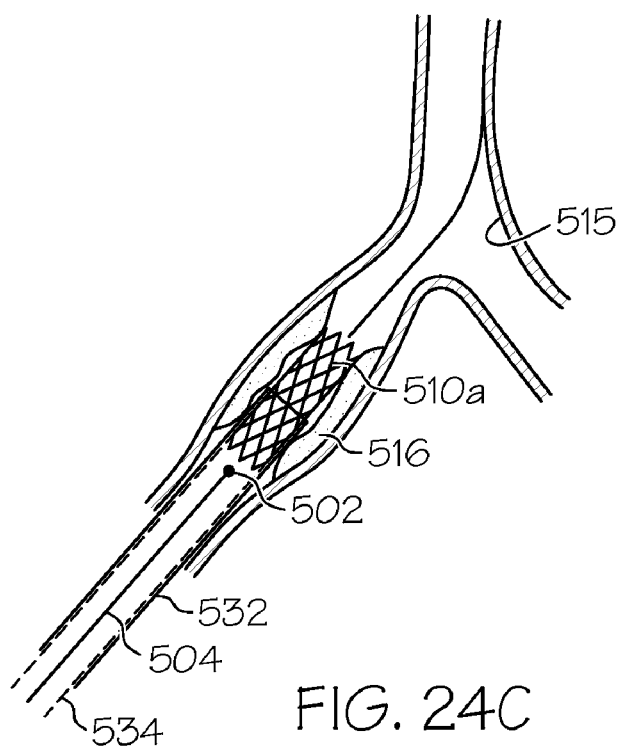

FIG. 23 shows a delivery catheter 500 onto which stent 510 may be mounted as taught in U.S. Pat. No. 5,649,952. In one embodiment, the delivery catheter 500 may be a conventional balloon dilatation catheter for angioplasty procedures. In another embodiment, the delivery catheter 500 may be a stent introducer as shown in FIG. 24A and taught in U.S. Pat. No. 5,545,211. The delivery catheter 500 may include connecting cable 504 and scanning module 502, as shown in FIG. 23 and FIGS. 24B-24C. Scanning module 502 is a portion of scanning beam assembly 1, which in some embodiments includes scanner assembly 2 within the central void 61 of housing 62 including collectors 3 (shown in FIG. 8). These example embodiments allow a clinician to see or visualize the site where the stent is to be placed. Once visually determined that the stent is in the desired position, the clinician may activate the stent using a therapeutic beam, laser, or one or more wavelengths of radiation that emits from scanning module 502.

Stent 510 may be an angioplasty stent for use in the coronary artery, femoral artery, renal artery, or carotid artery, or a renal stent for use in the ureter, or a biliary tree stent for use in the biliary duct, or a prostatic stent for use in the urethra, or a transjugular intrahepatic portosystemic shunt for use in the hepatic portal veins, or any other stent for treating a tubular passageway within the body.

In FIG. 23, balloon 514 may be attached to one end of a catheter body 520. The balloon 514 may be formed of suitable materials as described above for the first and second balloons 346 and 350 of FIG. 13. In order for the stent 510 to remain in place on the balloon 514 during delivery to the site of the damage within a body passageway 515, the stent 510 may be compressed onto the balloon 514, or protected by an annular sleeve, secured using a collar or ridges, or any other securing means. The delivery catheter 500 is advanced within the body passageway 515 until the stent 510 is directly under the detached lining or obstructing material 516.

In FIGS. 24A-24C, the introducer comprises an inner tube 530 and a guide 532. The inner tube 530 helps the whole delivery catheter 500 to pass through the body passageway 515 smoothly. A stent 510 may be positioned between the guide 532 and the inner tube 530. The inner tube 530 is pulled out from the guide 532, and the stent 510 in its compressed shape is pushed toward the opening of the guide 532 by a pusher 534 until the stent 510 is directly under the detached lining, obstructing material 516, or desired position within the body passageway 515.

Stent 510 may be constructed as taught in U.S. Pat. No. 5,649,952, U.S. Pat. No. 5,545,211, U.S. Pat. No. 6,976,994, U.S. Pat. No. 6,974,472, or U.S. Pat. No. 7,035,777. In one embodiment the stent may be made of shape memory alloy, which may be manufactured by the methods taught in U.S. Pat. No. 7,112,302.

As used herein, the term "shape memory alloy" or SMA is broadly defined as a metal-based alloy having a reversible solid-state transformation typically known as a martensitic transformation. Such materials typically exhibit the shape-memory effect and superelasticity distinct from conventional metals and alloys. These materials may be ferrous or non-ferrous martensites. Such materials include, but are not limited to, iron-based alloys, copper-based alloys, and nickel-titanium alloys. Ferrous systems include, but are not limited, iron and at least one of manganese, silicon, chromium and nickel, such as iron-manganese-silicon alloys and iron-chromium-nickel alloys. Copper-based systems are typically derived from copper-zinc, copper-aluminum, and copper-tin systems. Copper systems include, but are not limited to, copper and at least one of zinc, aluminum and nickel, such as copper-zinc-aluminum alloys, copper-nickel-aluminum alloys, and copper-beryllium-aluminum alloys. Nickel based systems include, but are not limited to nickel and at least one of titanium, copper, niobium, palladium, zirconium, and hafnium.

Figure 24D:
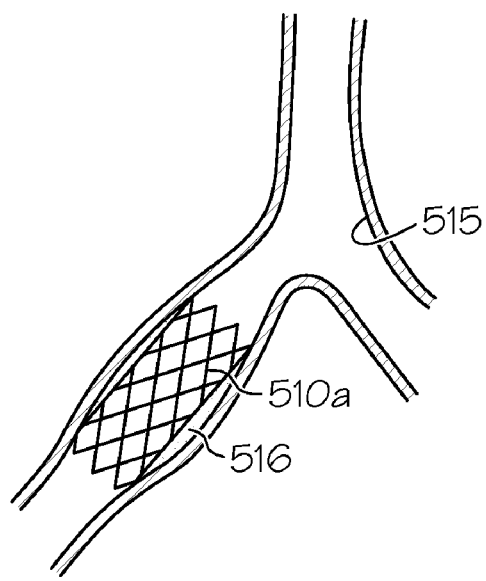

Stent 510 made of any of the above SMAs may have two distinct geometries that are temperature dependent. The metal may be configured in a first geometry 510a, as shown in FIGS. 24B,24C, at low temperatures, but will transition to a second geometry 510b at higher temperatures, as shown in FIG. 24D. The first geometry 510a may be a compressed state of small diameter, which is convenient for delivering the stent using the delivery catheter. The second geometry 510b may be an expanded state that conforms to the body passageway 515 as shown in FIG. 24D.

Figure 16:
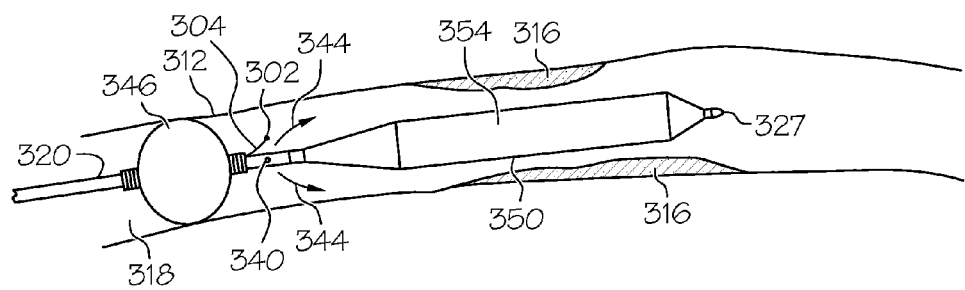
FIG. 16 is a perspective view of the balloon catheter of FIG. 13 shown with the scanning module external to the first and second balloon.

The transition from the compressed first geometry 510a, a low temperature state, to an expanded second geometry 510b, a higher temperature state, may occur after heating the SMA by exposing the SMA stent 510 to radiation emitting from the scanning module 302. Since stents are heat sensitive, a therapeutic beam or other radiation that may supply a safe amount of heat may be used to transition the stent 510 from the compressed first geometry 510a to the expanded second geometry 510b. In one embodiment the laser light may be emitted from the scanning module 302 of the scanning beam assembly 1. In one embodiment as shown in FIG. 23 the scanning module 302 may be inside the balloon 514. In another embodiment the scanning module 302 may be external to the balloon as similarly illustrated in FIG. 16.

In another embodiment, like those shown in FIGS. 24A-24D, the connecting cable 504 may extend through the pusher 534, thus placing the scanning module 502 inside the guide 532. The scanning module 502 may be moved forward such that the scanning module 502 is inside the first compressed geometry 510a of the stent 510. While inside the stent 510 the scanning module 502 may be set to selectively scan the SMA to activate the expansion thereof. The selective scan may be set by the clinician using the scanning beam assembly 1 as described above. In yet another embodiment, as shown in FIG. 24C, the scanning module 502 and the connecting cable are within the pusher 534. The end of the pusher 534 closest to the stent 510 may be made of a material that will allow the radiation from the laser light to pass through, or the material may have an opening or plurality of openings that allow the laser light to pass through to activate the SMA stent 510.

In another embodiment the SMA stent 510 may be wrapped in a mesh as taught in U.S. Pat. No. 5,545,211. The mesh may contain or be made of a radiation-responsive agent, a medical healing aide, or other treatment drug. The radiation-responsive agent may be radiation curable. The radiation curable radiation-responsive agent may be cured by exposure to the radiation emitted from the scanning module 502 as described above.

In another embodiment, the present invention includes a method for repairing or modifying an area of a patient's anatomy includes the steps of directing at least a portion of a scanning beam assembly to an area of a patient's anatomy, displaying an image of the anatomy, identifying a portion of the anatomy where radiation can be used to open a channel within a portion of the anatomy, and emitting the radiation to make the channel. The area of the anatomy may be the heart. Channels may be made into the heart (e.g., the wall of the heart) to isolate electrical signals. These channels may be used to treat arrhythmia or cause revascularization. In one embodiment, the scanning beam assembly may be simply used to visualize or image the making of the channel. In another embodiment, the scanning beam assembly may emit radiation that is capable of removing or making a channel opening through an occlusion within a lumen or organ of the body.

In one embodiment, the scanning beam assembly may be used to visualize or image a patient's anatomy. The scanning beam assembly may be used to image any medical procedure. In one embodiment, the assembly may be used to image the placement of stents or grafts within the body.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the assembly and method of the present invention has been illustrated in relation to repairing a site with a body using a scanning beam assembly, but it will be understood the present invention has applicability to other uses of a scanning beam assembly. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed is:

1. A method for repairing or modifying an area of a patient's anatomy comprising the steps of:
   (a) directing at least a portion of a scanning beam assembly to an area of a patient's anatomy, the scanning beam assembly comprising:
   a radiation source capable of emitting radiation;
   an optical fiber for directing the radiation from the radiation source toward a distal end of the scanning beam assembly in the form of a beam;
   a reflector that receives the beam of radiation from the optical fiber to direct the radiation onto the anatomy, wherein the reflector oscillates in at least two directions to create a scan of the anatomy with the radiation, the scan including sinusoidal angular deflections of the reflector yielding a bi-resonant or bi-sinusoidal scan path;
   a detector to detect radiation returned from the anatomy; and
   a controller to convert the detected radiation into a displayable image of the anatomy that was scanned by the radiation directed thereto by the reflector; wherein the controller comprises an interface management component that is electrically coupled to a user interface, the reflector, and the radiation source, wherein the interface management component upon receipt of specified treatment parameters transmits signals to a source control to drive the radiation source to provide a requisite emitting radiation output during the bi-resonant or bi-sinusoidal scan path;

(b) applying a radiation-responsive agent to a portion of the anatomy;

(c) exposing the radiation-responsive agent to radiation directed onto the agent by the reflector to cause the agent to therapeutically interact with the site;

(d) imaging the anatomy using the scanning beam assembly;

(e) displaying an image of the anatomy including the agent;

(f) using the displayed image of the anatomy to plan the placement of the radiation-responsive agent; and (g) selecting a treatment path where the reflector will direct therapeutic radiation for exposing the radiation-responsive agent.

2. The method of claim 1 wherein the area of the anatomy is selected from the group consisting of the stomach, colon, large or small intestine, ureter, urethra, biliary duct, artery, vein, abdominal cavity, esophagus, trachea, bronchial tubes, external tissue, internal tissue, and lumen.

3. The method of claim 1 wherein the portion of the anatomy is a tissue separation.

4. The method of claim 3 wherein the tissue separation is a surgical incision.

5. The method of claim 3 wherein the agent therapeutically interacts with the site to bond the tissue on each side of the incision together.

6. The method of claim 3 wherein the agent includes at least one of albumin, collagen, gelatin, curing aides, medicines, and healing aides to crosslink the tissue at the tissue separation.

7. The method of claim 1 wherein the agent is at least one of a paste, a gelatin, a liquid, a solid, a ribbon, a mesh, a film, a graft, a stent and a powder.

8. The method of claim 1 wherein the agent is a layer on a film, tape mesh, graft, or annular sleeve.

9. The method of claim 1 wherein the agent is cured by the radiation.

10. The method of claim 1 wherein the agent is bioabsorbable.

11. The method of claim 1 wherein the agent is a medical adhesive.

12. The method of claim 11 wherein the medical adhesive includes at least one of albumin, collagen, gelatin, curing aides, medicines, and healing aides.

13. The method of claim 1 wherein the agent is a medical drug.

14. The method of claim 1 wherein applying the radiation-responsive agent comprises directing an applicator through a channel of a medical instrument to the selected area of the anatomy.

15. The method of claim 14 wherein exposing the radiation-responsive agent to radiation forms a stent from the applied radiation-responsive agent.

16. The method of claim 15 wherein the stent includes slots made by selectively curing the radiation-responsive agent.

17. The method of claim 1 wherein exposing the agent with radiation is done to selectively cure a portion of the applied agent.

18. The method of claim 1 wherein the portion of the scanning beam assembly being directed to the anatomy includes a medical guidewire.

19. The method of claim 1 wherein the scanning beam assembly further comprises a collector that intercepts the radiation returned from the anatomy and passes the radiation to the detector.

20. The method of claim 19 wherein the collector includes a plurality of multimode collecting fibers.

21. The method of claim 19 wherein the scanning beam assembly further comprises a housing enclosing the collector and the reflector, wherein the housing is insertable within an area of the anatomy.

22. The method of claim 20 wherein the scanning beam assembly further comprises a housing enclosing the collector and the reflector, wherein the housing is insertable within an area of the anatomy.

23. The method of claim 1 wherein the radiation returned from the anatomy is radiation reflected from the scanned portion of the anatomy.

24. An intraluminal vascular graft made according to the method of claim 23.

25. The method of claim 23 wherein the portion of the scanning beam assembly is directed to the area of the body as part of a balloon catheter, wherein a quantity of the radiation-responsive agent is applied onto the balloon, and the balloon is expanded to apply the agent to the site.

26. The method of claim 25 wherein the radiation-responsive agent is dispensed onto the balloon from an infusion port within the balloon catheter.

27. The method of claim 25 wherein the radiation-responsive agent is applied to the balloon before the catheter is directed to the portion of the anatomy.

28. The method of claim 27 wherein the radiation-responsive agent is applied to the balloon as at least one of a coating, a film, and an annular sleeve.

29. The method of claim 28 wherein the annular sleeve is a mesh with a coating of a medical adhesive.

30. The method of claim 28 wherein the balloon has a cover to protect the radiation-responsive agent while the catheter is directed toward the portion of the anatomy.

31. The method of claim 23 wherein exposing the radiation-responsive agent lo radiation forms a stent from the applied radiation-responsive agent.

32. The method of claim 31 wherein the radial ion-responsive agent is bioabsorbable.

33. The method of claim 31 wherein the stent has tubular walls of uniform thickness.

34. The method of claim 31 wherein the stent includes slots made by selectively curing the radiation-responsive agent.

35. The method of claim 31 wherein the stent is made to a custom length by repealing the method as the catheter is moved along the area of the body.

36. The method of claim 23 wherein the radiation-responsive agent is a shape memory alloy.

37. The method of claim 36 wherein the shape memory alloy is a stent assembly.

38. The method of claim 37 wherein the stent is applied by a catheter.

39. The method of claim 36 wherein the shape memory alloy is at least one of a nickel based alloy, a nickel titanium alloy, and a copper based alloy.

40. A balloon catheter comprising:

(a) an expandable balloon:

(b) a catheter body having a plurality of lumens, wherein at least one lumen opens into the interior of the expandable balloon; and (c) at least a portion of a scanning beam assembly, the scanning beam assembly comprising;

a radiation source capable of emitting radiation;

a reflector that receives the radiation from the radiation source to direct the radiation onto a patient's anatomy, wherein the reflector oscillates in at least two directions to create a scan of the anatomy;

a detector to detect radiation returned from the anatomy; and a controller to convert the detected radiation into a displayable image of the anatomy; wherein the controller comprises an interface management component that is electrically coupled to a user interface, the reflector, and the radiation source, wherein the interface management component upon receipt of specified treatment parameters transmits signals to a source control to drive the radiation source to provide a requisite emitting radiation output for said treatment parameters.

41. The balloon catheter of claim 40 wherein the portion of the scanning beam assembly is fed through the lumen that opens into the interior of the expandable balloon.

42. The balloon catheter of claim 40 further comprising:
(d) an infusion port for dispensing a radiation-responsive agent, the infusion port connected to at least one lumen within the catheter body.

43. The balloon catheter of claim 40 wherein the expandable balloon is made of a material that can transmit the radiation from the reflector through the balloon.

44. The balloon catheter of claim 40 wherein at least one lumen exits the catheter body near the proximal end of the expandable balloon.

45. The balloon catheter of claim 44 wherein the scanning beam portion of the scanning beam assembly is fed through the lumen that exits the catheter body near the proximal end of the expandable balloon.

46. A method for repairing or modifying an area of a patient's anatomy comprising the steps of:
(a) directing at least a portion of a scanning beam assembly to an area of a patient's anatomy, the scanning beam assembly comprising:
  a radiation source capable of emitting radiation;
  an optical fiber for directing the radiation from the radiation source toward a distal end of the scanning beam assembly in the form of a beam;
  a reflector that receives the beam of radiation from the optical fiber to direct the radiation onto the anatomy, wherein the reflector oscillates in at least two directions to create a scan of the anatomy with the radiation, the scan including sinusoidal angular deflections of the reflector yielding a bi-resonant or bi-sinusoidal scan path;
  a detector to detect radiation returned from the anatomy; and
  a controller lo convert the detected radiation into a displayable image of the anatomy that was scanned by the radiation directed thereto by the reflector; wherein the controller comprises an interface management component that is electrically coupled to a user interface, the reflector, and the radiation source, wherein the interface management component upon receipt of specified treatment parameters from a user transmits signals a source control to drive the radiation source to provide the requisite emitting radiation output for said treatment parameters:
  wherein the radiation is itself capable of making a channel into an organ or is itself capable of removing or making a channel opening through an occlusion within a lumen or organ;
(b) displaying an image of the anatomy that includes the lumen or organ;
(c) identifying where the radiation is to open a channel within a portion of the lumen or organ; and
(d) emitting the radiation to make the channel.

47. The method of claim 46 wherein the organ is the heart.

48. The method of claim 47 wherein the channel is made in the wall of the heart.

* * * * *